(12) United States Patent
McAdams et al.

(10) Patent No.: US 9,004,918 B2
(45) Date of Patent: Apr. 14, 2015

(54) COMPOSITIONS, ASSEMBLIES, AND METHODS APPLIED DURING OR AFTER A DENTAL PROCEDURE TO AMELIORATE FLUID LOSS AND/OR PROMOTE HEALING, USING A HYDROPHILIC POLYMER SPONGE STRUCTURE SUCH AS CHITOSAN

(75) Inventors: Staci Ann McAdams, Milwaukie, OR (US); William David Block, Lake Oswego, OR (US); Simon John McCarthy, Portland, OR (US); Kenton W. Gregory, Portland, OR (US); Hal Oien, Tualatin, OR (US)

(73) Assignee: HemCon Medical Technologies, Inc., Portland, OR (US)

( * ) Notice: Subject to any disclaimer, the term of this patent is extended or adjusted under 35 U.S.C. 154(b) by 509 days.

(21) Appl. No.: 12/804,010

(22) Filed: Jul. 12, 2010

(65) Prior Publication Data
US 2011/0143312 A1    Jun. 16, 2011

Related U.S. Application Data

(63) Continuation of application No. 12/592,124, filed on Nov. 19, 2009, now abandoned, which is a continuation-in-part of application No. 11/261,351, filed on Oct. 28, 2005, now Pat. No. 7,897,832, which (Continued)

(51) Int. Cl.
*A61F 13/00* (2006.01)
*A61C 19/06* (2006.01)
(Continued)

(52) U.S. Cl.
CPC ......... *A61L 15/425* (2013.01); *A61F 13/00012* (2013.01); *A61F 13/00034* (2013.01); *A61F 13/00987* (2013.01); *A61F 13/00995* (2013.01); *A61F 13/15203* (2013.01); *A61F 2013/00106* (2013.01); *A61F 2013/00463* (2013.01); *A61F 2013/00468* (2013.01); *A61F 2013/00472* (2013.01); *A61F 2013/00536* (2013.01);
(Continued)

(58) Field of Classification Search
None
See application file for complete search history.

(56) References Cited

U.S. PATENT DOCUMENTS

| 2,610,625 A | 9/1952 | Sifferd et al. |
| 2,858,830 A | 11/1958 | Robins |

(Continued)

FOREIGN PATENT DOCUMENTS

| EP | 0353972 | 2/1990 |
| EP | 0477979 | 9/1991 |

(Continued)

OTHER PUBLICATIONS

Park et al., Platelet derived growth factor releasing chitosan sponge for periodontal bone regeneration, Biomaterials 21 (2000) 153-159.*
(Continued)

*Primary Examiner* — Peter J Reddig
*Assistant Examiner* — Sarah Chickos
(74) *Attorney, Agent, or Firm* — Miller Nash LLP; Chandra E. Eidt

(57) ABSTRACT

Dental dressing assemblies are formed from hydrophilic polymer sponge structures, such as a densified chitosan biomaterial. The invention also contemplates systems and methods that can be used in conjunction with stents and periodontal dressings to promote hemostasis and secondary healing in free gingival graft palatal donor sites and all other oral and maxillofacial surgical sites.

16 Claims, 11 Drawing Sheets

Related U.S. Application Data is a continuation-in-part of application No. 10/743,052, filed on Dec. 23, 2003, now Pat. No. 7,371,403, which is a continuation-in-part of application No. 10/480,827, filed as application No. PCT/US02/18757 on Jun. 14, 2002, now Pat. No. 7,482,503.

(60) Provisional application No. 60/298,773, filed on Jun. 14, 2001.

(51) Int. Cl.
 A61L 33/08 (2006.01)
 A61L 15/28 (2006.01)
 A61L 15/16 (2006.01)
 A61L 15/42 (2006.01)
 A61F 13/15 (2006.01)

(52) U.S. Cl.
 CPC .............. A61F2013/0054 (2013.01); A61F 2013/00931 (2013.01); A61L 15/28 (2013.01); A61L 2400/04 (2013.01)

(56) References Cited

U.S. PATENT DOCUMENTS

| | | |
|---|---|---|
| 2,923,664 A | 2/1960 | Cook et al. |
| 3,551,556 A | 12/1970 | Kliment et al. |
| 3,632,754 A | 1/1972 | Balassa |
| 3,800,792 A | 4/1974 | McKnight et al. |
| 3,801,675 A | 4/1974 | Russell |
| 3,849,238 A | 11/1974 | Gould et al. |
| 3,902,497 A | 9/1975 | Casey |
| 3,911,116 A | 10/1975 | Balassa |
| 3,954,493 A | 5/1976 | Battista et al. |
| 3,977,406 A | 8/1976 | Roth |
| 4,040,884 A | 8/1977 | Roth |
| 4,056,103 A | 11/1977 | Kaczmarzyk et al. |
| 4,068,757 A | 1/1978 | Casey |
| 4,094,743 A | 6/1978 | Leuba |
| 4,195,175 A | 3/1980 | Peniston et al. |
| 4,292,972 A | 10/1981 | Pawelchak et al. |
| 4,373,519 A | 2/1983 | Errede et al. |
| 4,394,373 A | 7/1983 | Malette et al. |
| 4,452,785 A | 6/1984 | Malette et al. |
| 4,460,642 A | 7/1984 | Errede et al. |
| 4,501,835 A | 2/1985 | Berke |
| 4,524,064 A | 6/1985 | Nambu |
| 4,532,134 A | 7/1985 | Malette et al. |
| 4,533,326 A * | 8/1985 | Anthony .................. 433/229 |
| 4,541,426 A | 9/1985 | Webster |
| 4,599,209 A | 7/1986 | Dautzenberg et al. |
| 4,651,725 A | 3/1987 | Kifune et al. |
| 4,684,370 A * | 8/1987 | Barrett .................. 623/16.11 |
| 4,699,135 A | 10/1987 | Motosugi et al. |
| 4,759,348 A | 7/1988 | Cawood |
| 4,772,419 A | 9/1988 | Malson et al. |
| 4,833,237 A | 5/1989 | Kawamura et al. |
| 4,948,540 A | 8/1990 | Nigam |
| 4,952,618 A | 8/1990 | Olsen |
| 4,956,350 A | 9/1990 | Mosbey |
| 4,958,011 A | 9/1990 | Bade |
| 4,960,413 A | 10/1990 | Sagar et al. |
| 4,973,493 A | 11/1990 | Guire |
| 4,977,892 A | 12/1990 | Ewall |
| 5,006,071 A | 4/1991 | Carter |
| 5,024,841 A | 6/1991 | Chu et al. |
| 5,035,893 A | 7/1991 | Shioya et al. |
| 5,062,418 A | 11/1991 | Dyer et al. |
| 5,110,604 A | 5/1992 | Chu et al. |
| 5,116,824 A | 5/1992 | Miyata et al. |
| 5,154,928 A | 10/1992 | Andrews |
| 5,206,028 A | 4/1993 | Li |
| 5,252,275 A * | 10/1993 | Sultze et al. .................. 264/119 |
| 5,254,301 A | 10/1993 | Sessions et al. |
| 5,300,494 A | 4/1994 | Brode, II et al. |
| 5,376,376 A | 12/1994 | Li |
| 5,378,472 A | 1/1995 | Muzzarelli |
| 5,420,197 A | 5/1995 | Lorenz et al. |
| 5,454,719 A | 10/1995 | Hamblen |
| 5,525,710 A | 6/1996 | Unger et al. |
| 5,571,181 A * | 11/1996 | Li .............................. 623/23.75 |
| 5,597,581 A | 1/1997 | Kaessmann et al. |
| 5,643,596 A | 7/1997 | Pruss et al. |
| 5,700,476 A | 12/1997 | Rosenthal et al. |
| 5,738,860 A * | 4/1998 | Schønfeldt et al. ........... 424/402 |
| 5,756,111 A | 5/1998 | Yoshikawa et al. |
| 5,797,960 A | 8/1998 | Stevens et al. |
| 5,821,271 A | 10/1998 | Roenigk |
| 5,827,265 A | 10/1998 | Glinsky et al. |
| 5,836,970 A | 11/1998 | Pandit |
| 5,840,777 A | 11/1998 | Eagles et al. |
| 5,858,292 A | 1/1999 | Dragoo et al. |
| 5,858,350 A | 1/1999 | Vournakis et al. |
| 5,952,618 A | 9/1999 | Deslauriers |
| 5,961,478 A | 10/1999 | Timmermans |
| 6,042,877 A | 3/2000 | Lyon et al. |
| 6,054,122 A | 4/2000 | MacPhee et al. |
| 6,103,369 A | 8/2000 | Lucast et al. |
| 6,124,273 A | 9/2000 | Drohan et al. |
| 6,156,330 A | 12/2000 | Tsukada et al. |
| 6,162,241 A | 12/2000 | Coury et al. |
| 6,225,521 B1 | 5/2001 | Gueret |
| 6,270,515 B1 | 8/2001 | Linden et al. |
| 6,406,712 B1 | 6/2002 | Rolf |
| 6,448,462 B2 | 9/2002 | Groitzsch et al. |
| 6,454,787 B1 | 9/2002 | Maddalo et al. |
| 6,485,667 B1 | 11/2002 | Tan |
| 6,486,285 B2 | 11/2002 | Fujita |
| 6,548,569 B1 | 4/2003 | Williams et al. |
| 6,552,244 B1 | 4/2003 | Jacques et al. |
| 6,565,878 B2 | 5/2003 | Schoenfeldt et al. |
| 6,566,577 B1 | 5/2003 | Addison et al. |
| 6,599,891 B2 | 7/2003 | North et al. |
| 6,693,180 B2 | 2/2004 | Lee et al. |
| 6,726,712 B1 | 4/2004 | Raeder-Devens et al. |
| 6,855,860 B2 | 2/2005 | Ruszczak et al. |
| 6,863,924 B2 | 3/2005 | Ranganathan et al. |
| 6,864,245 B2 | 3/2005 | Vournakis et al. |
| 6,992,233 B2 | 1/2006 | Drake et al. |
| 7,019,191 B2 | 3/2006 | Looney et al. |
| 7,371,403 B2 | 5/2008 | McCarthy et al. |
| 7,402,172 B2 | 7/2008 | Chin et al. |
| 7,546,812 B2 | 6/2009 | Eastin et al. |
| 7,637,934 B2 | 12/2009 | Mangiardi et al. |
| 7,671,102 B2 | 3/2010 | Gaserod et al. |
| 7,820,872 B2 | 10/2010 | Gregory et al. |
| 7,850,709 B2 | 12/2010 | Cummins et al. |
| 7,897,832 B2 | 3/2011 | McAdams et al. |
| 8,063,265 B2 | 11/2011 | Beck et al. |
| 2001/0045177 A1 | 11/2001 | Harvey et al. |
| 2002/0071855 A1 | 6/2002 | Sadozai et al. |
| 2002/0161376 A1 | 10/2002 | Barry et al. |
| 2004/0243043 A1 | 12/2004 | McCarthy et al. |
| 2005/0036955 A1 | 2/2005 | DeGould |
| 2005/0038369 A1 | 2/2005 | Gregory et al. |
| 2005/0123581 A1 | 6/2005 | Ringeisen et al. |
| 2005/0137512 A1 | 6/2005 | Campbell et al. |
| 2005/0147656 A1 | 7/2005 | McCarthy et al. |
| 2005/0240137 A1 | 10/2005 | Zhu et al. |
| 2006/0004314 A1 | 1/2006 | McCarthy et al. |
| 2006/0008419 A1 | 1/2006 | Hissink et al. |
| 2006/0083710 A1 | 4/2006 | Joerger et al. |
| 2006/0184224 A1 | 8/2006 | Angel |
| 2006/0211973 A1 | 9/2006 | Gregory et al. |
| 2007/0021703 A1 | 1/2007 | McCarthy |
| 2007/0066920 A1 | 3/2007 | Hopman et al. |
| 2007/0083137 A1 | 4/2007 | Hopman et al. |
| 2007/0237811 A1 | 10/2007 | Scherr |
| 2007/0255194 A1 | 11/2007 | Gudnason et al. |
| 2007/0255243 A1 | 11/2007 | Kaun et al. |
| 2007/0276308 A1 | 11/2007 | Huey et al. |
| 2008/0132990 A1 | 6/2008 | Richardson |

(56) References Cited

U.S. PATENT DOCUMENTS

| | | | |
|---|---|---|---|
| 2008/0147019 A1 | 6/2008 | Song et al. | |
| 2008/0241229 A1 | 10/2008 | Li et al. | |

FOREIGN PATENT DOCUMENTS

| | | |
|---|---|---|
| EP | 0643963 A2 | 4/1994 |
| EP | 1462123 | 9/2004 |
| JP | 60-142927 | 7/1985 |
| JP | 62-039506 | 2/1987 |
| JP | 60-090507 | 4/1988 |
| JP | 63-090507 | 4/1988 |
| JP | 07-116241 | 5/1995 |
| JP | 11-342153 | 12/1999 |
| JP | 2002-233542 | 8/2002 |
| WO | WO 95/05794 | 3/1995 |
| WO | WO 99/02587 | 1/1999 |
| WO | WO 00/56256 | 9/2000 |
| WO | WO 02/102276 | 12/2002 |
| WO | WO 03/047643 | 6/2003 |
| WO | WO 03/079946 | 10/2003 |
| WO | WO 03/092756 | 11/2003 |
| WO | WO 03/101310 | 12/2003 |
| WO | WO 2004/047695 | 6/2004 |
| WO | WO 2004/060412 | 7/2004 |
| WO | WO 2005062880 | 7/2005 |
| WO | WO 2006049463 | 5/2006 |
| WO | WO 2006071649 | 7/2006 |
| WO | WO 2007009050 | 1/2007 |
| WO | WO 2007056066 | 5/2007 |
| WO | WO 2007074327 | 7/2007 |
| WO | WO 2008033462 | 3/2008 |
| WO | WO 2008036225 | 3/2008 |

OTHER PUBLICATIONS

Allan et al,, "Biomedical Applications of Chitin and Chitosan." Chitin, Chitosan, and Related Enzymes—Accademic Press, Inc.: 119-133, 1984.
Anema et al., "Poental Uses of Absobable Fibrin Adhesive Bandage for Genitourinary Trauma." World Journal of Surgery, vol. 25: 1573-1577, 2001.
Bégin et al., "Antimicrobial films produced from chitosan." International Journal of Biological Macromolecules, vol. 26: 63-67, 1999.
Belman et al,, "From the Battlefield to the Street," Per declaration submitted in U.S. Appl. No. 10/480,827, dated Dec. 17, 2007, poster presentation was made at the ATACCC Conference, Aug. 2006.
CNN Transcript—3pp., Jun. 8, 2006.
HemCon Manufacturing Materials. Per declaration submitted in U.S. Appl. No. 10/480,827, dated Dec. 17, 2007, materials were submitted as supporting evidence for declaration.
Horesh et al., "Pre-hospital use of the HemCon bandage," Per declaration submitted in U.S. Appl. No. 10/480,827, dated Dec. 17, 2007, poster presentation was made at the WCDEM Conference, May 2007.
Kiley, Kevin, "Department of the Army memo." Jul. 20, 2005.
Kumar, Ravi, "Chitin and chitosan fibres: A review." Bulletin of Material Science: vol. 22, No, 5: 905-915, Aug. 1999.
Luo et al., "The role of poly(ethylene glycol) in the formation of silver nanoparticles." Journal of Colloid and Interface Science, vol. 288: 444-448, 2005.
Martin et al., "Medical application of poly-4-hydroxybutyrate: a strong flexible absorbable biomaterial." Biochemical Engineering Journal, vol. 16: 97-105, 2003.
Moody, Robin J., "HemCon bandage stakes claim to soldier's kit bag." Portland Business Journal, Nov. 4, 2005.
Ohshima et al., "Clinical Application of Chitin Non-Woven Fabric as Wound Dressing." European Journal of Plastic Surgery, vol. 10: 66-69, 1987.
Oshima et al., "Clinical application of new chitin non-woven fabric and new chitin sponge sheet as wound dressing." European Journal of Plastic Surgery, vol. 14: 207-211, 1991.
Percot et al., "Optimization of Chitin Extraction from Shrimp Shells." Biomacromolecules, vol. 4: 12-18, 2003.
Pusateri et al., "Advanced Hemostatic Dressing Development Program: Animal Model Selection Criteria and Results of a Study of Nine Hemostatic Dressings in a Model of Severe Large Venous Hemorrhage and Hepatic Injury in Swine." The Journal of Trauma, vol. 55: 518-526, 2003.
Sandford, Paul A., "Chitosan: Commercial Uses and Potential Applications." Chitin and Chitosan: Proceedings from the 4th International Conference on Chitin and Chitosan, 51-69, 1988.
Sandford, Paul A., "Biomedical Applications of New Forms of Chitin/Chitosan." Chitin Derivatives in Life Science, 12pp., 1992.
Siekman, Philip, "A Shrimp Bandage?" Fortune Small Business, pp. 67-68, 2006.
Sondeen et al., "Comparison of 10 Different Hemostatic Dressings in an Aortic Injury." The Journal of Trauma, vol. 54, No. 2: 280-285, 2003.
Wedmore et al., "A Special Report on the Chitosan-based Hemostatic Dressing: Experience in Current Combat Operations." The Journal of Trauma, vol. 60: 655-658, 2006.
Wilson, J,R., "The Army's Greatest Inventions." U.S. Army Materiel Command, pp. 30-37, 2005.
Fwu-Long Mi et al., "*Fabrication and characterization of a sponge-like asymmetric chitosan membrane as a wound dressing.*" Biomaterials 22 pp. 165-173 (2001), Elsevier Science Ltd., London and New York.
Michele W. Chan et al., "*Comparison of Poly-N-acetyl Glucosamine (P-GlcNAc) with Absorbable Collagen (Actifoam), and Fibrin Sealant (Bolheal) for Achieving Hemostatis in a Swine Model of Splenic Hemorrhage.*"The Journal of Trauma 48(3) pp. 454-458 (2000) Lippincott Williams & Wilkins, Inc. U.S.A.
Paul A. Sanford et al., "*Biomedical Applicants of High-Purity Chitosan*," ACS Symposium Series 467 pp. 430-445 (1991) American Chemical Society, Washington D.C.
William G. Malette et al., "*Chitosan: A New Hemostatic*," The Annals of Thoracic Surgery 36(1) pp. 55-58 (1983).
Roger Olsen et al., "*Biomedical Applicants of Chitin and Its Derivatives*," Chitin and Chitosan pp. 813-829 (1988) Elsevier Applied Science, London and New York.
David J. Cole et al., "*A pilot study evaluating the efficacy of a fully acetylated ply-N-acetyl glucosamine membrane formulation as a topical hemostatic agent*," Surgery 126(3) pp. 510-517 (1999) Mosby, Inc. U.S.A.
Bendix., "Chemical synthesis of polyactide and its copolymers for medical applications." Polymer Degradation and Stability, vol. 59: 129-135, 1998.
Schoof et al., "Control of Pore Structure and Size in Freeze-Dried Collagen Sponges." Journal of Biomedical Material Research, vol. 58: 352-357, 2001.
Wu et al., "Development of In Vitro Adhesion Test for Chitosan Bandages." Society for Biomaterials 30th Annual Meeting Transactions, 2005, 1 pg.
Database WPI, Week 200873 Thomson Scientific, London GB, AN 2008-M34232, XP002695569 & CN 101138648, Mar. 12, 2008.

* cited by examiner

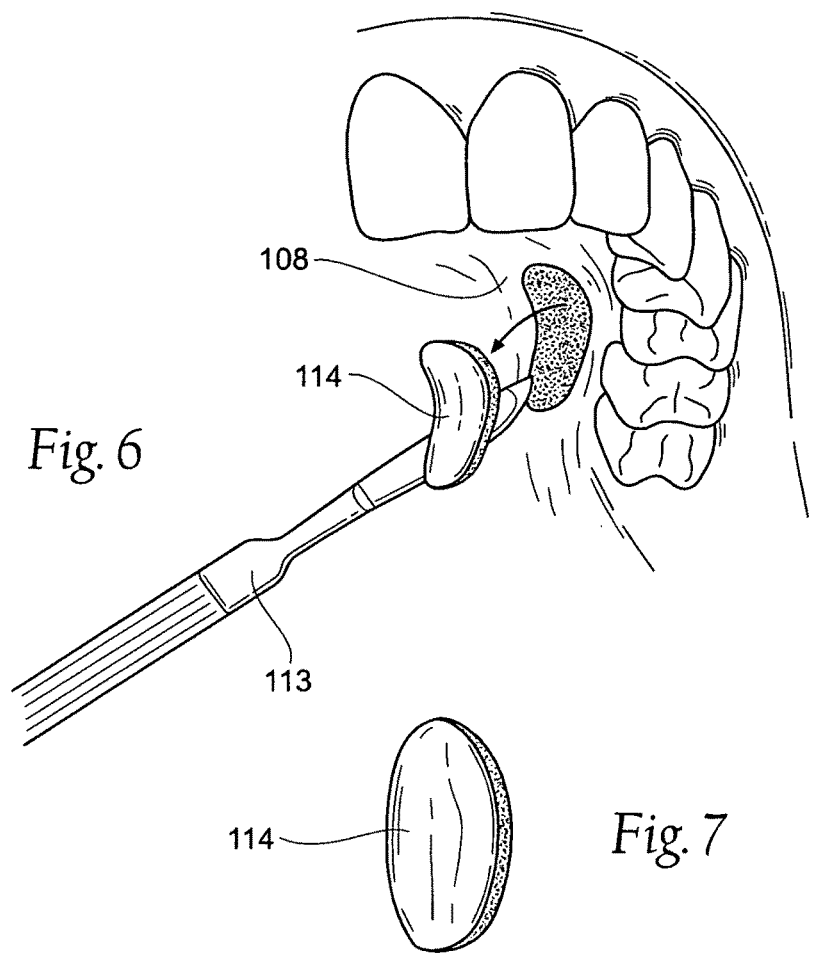
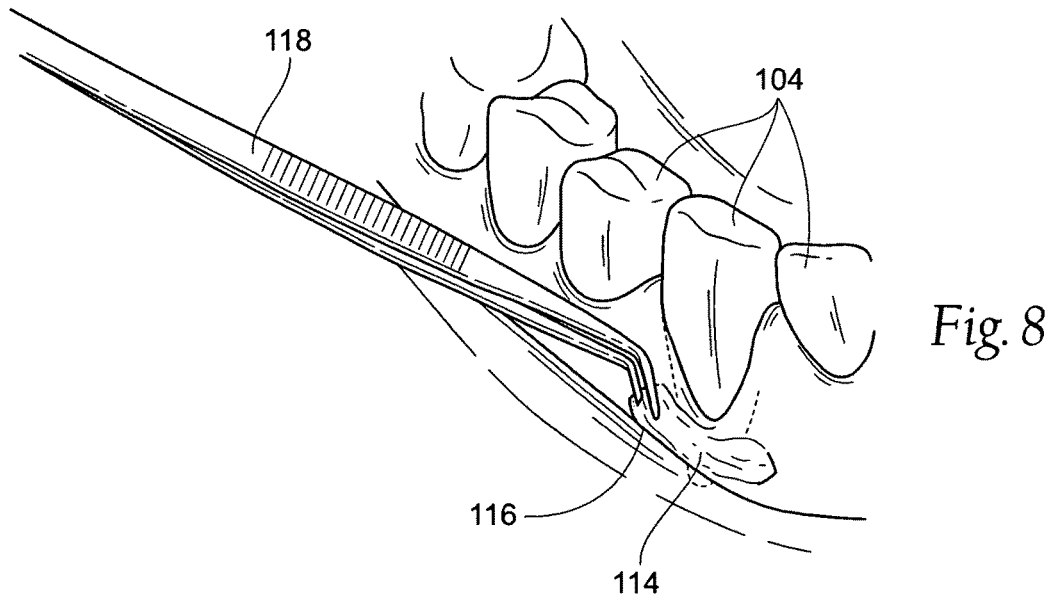

COMPOSITIONS, ASSEMBLIES, AND METHODS APPLIED DURING OR AFTER A DENTAL PROCEDURE TO AMELIORATE FLUID LOSS AND/OR PROMOTE HEALING, USING A HYDROPHILIC POLYMER SPONGE STRUCTURE SUCH AS CHITOSAN

RELATED APPLICATIONS

This application is a continuation of application Ser. No. 12/592,124 filed on Nov. 19, 2009, now abandoned, which is a continuation-in-part of U.S. patent application Ser. No. 11/261,351, filed on Oct. 28, 2005, issued as U.S. Pat. No. 7,897,832, which is a continuation-in-part of U.S. application Ser. No. 10/743,052, filed on Dec. 23, 2003, issued as U.S. Pat. No. 7,371,403, which is a continuation-in-part of U.S. patent application Ser. No. 10/480,827 filed Oct. 6, 2004, filed as International Application No. PCT/US02/18757 on Jun. 14, 2002, issued as U.S. Pat. No. 7,482,503, which claims the benefit of provisional patent application Ser. No. 60/298,773 filed Jun. 14, 2001. Each of these applications is incorporated herein by reference.

FIELD OF THE INVENTION

The invention is generally directed to compositions, assemblies, and methods applied during or after a dental procedure to ameliorate bleeding, fluid seepage or weeping, or other forms of fluid loss, as well as promote healing and to limit secondary problems associated with the dental procedures.

BACKGROUND OF THE INVENTION

FIG. 1 is an anatomic view of a healthy tooth. The tooth includes a crown and a root. The root is encased by a supporting ligament in alveolar (jaw) bone. The ligament comprises a tough band of shock-absorbing connective tissue, which physically binds the tooth root to the jaw bone. The hole occupied by the tooth in the bone is called the tooth socket.

The crown of the tooth is exposed above the gum. A hard shiny outer surface, called the enamel, covers the crown. Below the enamel is dentin, which is microscopically porous hard tissue. At the center of the tooth is the pulp chamber, which houses the pulp consisting of blood vessels and nerve tissues.

A tooth may become damaged, or decayed, e.g., due to erosion of the calcium in the tooth's enamel by bacteria. This, in turn, can lead to erosion of the dentin beneath the enamel. As the decay continues, bacteria can migrate through the porous dentin and infect the pulp. An immune response to the infection can follow, causing the blood vessels around the tooth to enlarge and press against the nerves entering the tooth. The result is tooth ache.

There are various dental procedures for intervening when these or other conditions affecting the oral cavity and its anatomic structures arise. These procedures are routinely performed by dentists including general practitioners, oral and maxillofacial surgeons, endodontists and periodontists.

For example, endodontic therapy, also called root canal therapy, can, under many circumstances, intervene to remove the bacteria, nerve tissue, organic debris, and bacterial toxins from within the inner aspects of a decaying tooth. Following this, the practitioner fills in and seals off the interior of the tooth. Currently, there are about 16 million root canals performed annually in the USA.

If the decay has progressed too far, removal or extraction of the tooth may be indicated. Currently, there are more than 30 million extractions performed each year in the USA. During a simple extraction, a dentist will grasp the tooth with an instrument, e.g., forceps, and rock the tooth back and forth. This rocking motion loosens the tooth from the alveolar bone by breaking the periodontal ligaments that hold the tooth in place. The tooth is then extracted from the socket, leaving the tooth socket open.

Removal or extraction of the tooth may also be indicated when the presence of the tooth is causing crowding, or malocclusion, or preventing another tooth (e.g., a wisdom tooth) from erupting, or in preparation for orthodontic treatment ("braces"). A tooth extraction may also be indicated because of advanced periodontal (gum) disease. Sometimes, if the tooth selected for extraction is not fully erupted above the gum, it may be necessary to first remove some of the overlying gum and bone tissue in order to access the tooth for extraction.

During and after such conventional dental procedures—e.g., endodontic surgery, or periodontal surgery, orthodontic treatment, tooth extractions, orthognathic surgery, biopsies, and other oral surgery procedures—bleeding, fluid seepage or weeping, or other forms of fluid loss typically occur. Bleeding, fluid seepage or weeping, or other forms of fluid loss can also occur in the oral cavity as a result of injury or trauma to tissue and structures in the oral cavity. In this regard, there are about two million teeth lost each year due to accidents. Swelling and residual bleeding can be typically expected to persist during the healing period following the procedure or injury. During the healing period, new gum tissue will grown into the gap left by the extraction.

It is thereby desirable during the healing period to take steps to stanch, seal, and/or stabilize the site of surgical intervention—or the site of tissue injury or trauma—against fluid loss due to bleeding, fluid seepage or weeping. During and after dental procedures or injury to the oral cavity, there is a need for quick and effective hemostasis.

For example, following a tooth extraction, the quick cessation of bleeding and the formation of a blood clot on the wound in the open tooth socket are very desirable. Indeed, during the entire healing period following an extraction—which can take from one to six weeks—it is important to preserve conditions conducive to hemostasis, so that the blood clot that forms within the socket does not break down and/or dislodge. If the clot breaks down and/or dislodges, a condition known as a dry socket (also called alveolar osteitis) results. Dry socket conditions can also occur for the same reason during the treatment of cystic cavity defects in the jaw. Dry socket can cause pain and discomfort, which will subside only as the socket heals through a secondary healing process.

Conventionally, cotton packs and rolled or folded cotton gauze pads are commonly used to stem the bleeding precipitated during and after dental procedures. While the presence of such materials may absorb blood and fluids, they do not promote or create conditions conducive to rapid and long term hemostasis or healing. There still remains a need for improved hemostatic compositions, assemblies, and methods that can be applied during or after dental procedures.

Along with damage to the tooth itself, there may also be damage to the gums and gingival material surrounding the tooth or teeth. For example, people may have problems associated with inadequate amounts of gingival material surrounding a tooth or teeth. If there is inadequate attached gingiva, spontaneous recession of the gum and bone will occur over time. Typically the normal attached gingiva has been worn away with improper brushing, although some people are born with very little attached gingiva.

Surgeries are performed on these areas to provide added gingiva to the area, typically by adding a gingival graft from another area located in the person's mouth. These procedures are frequently performed, yet they are also some of the most sensitive surgical wounds that must be managed by periodontists. Post operative pain, recurrent bleeding, delayed secondary healing, associated with these types of wounds and the open nature of these wounds all contribute to the problematic post operative issues associated with these types of wounds. Treatment generally has been done using protective stents and/or periodontal dressings placed over the wound area, but these treatments do not necessarily promote hemostasis and secondary healing for the wound site as effectively as desired. Consequently, there has been a long felt need for processes and assemblies that can be used to promote hemostasis, enhance blood clot stability after surgery and shorten healing times.

SUMMARY OF THE INVENTION

The invention provides assemblies, systems and methods for treating tissue or bone in an oral cavity or an adjacent anatomic structure, comprising the placement of a hydrophilic polymer sponge structure.

An aspect of the invention contemplates systems and methods that can be used in conjunction with stents and periodontal dressings to promote hemostasis and secondary healing in gingival surgery, such as surgery utilizing free gingival graft palatal donor sites. The systems and methods utilize hydrophilic polymer sponge structures that will be placed within the area that will receive the gingival graft material.

One aspect of the invention provides a hydrophilic polymer sponge structure that is shaped, sized, and configured for placement in association with tissue or bone in an oral cavity or an adjacent anatomic structure, as well as a method for placing the hydrophilic polymer sponge structure in association with the tissue or bone in the oral cavity or the adjacent anatomic structure.

Another aspect of the invention includes systems and methods for performing a dental surgical procedure, which can comprise, e.g., a tooth extraction; or endodontic surgery; or periodontal surgery; or orthodontic treatment; or orthognathic surgery; or a biopsy; or gingival surgery; or osseous surgery; or scaling or root planning; or periodontal maintenance; or complete maxillary or mandibular denture; or complete or partial denture adjustment; or denture rebase or reline; or soft tissue surgical extraction; or bony surgical extraction; or installation of an occlusal orthotic device or occlusal guard or occlusal adjustment; or oral surgery involving jaw repair; treatment of cystic cavity defects in the jaw; or new bone growth or bone growth promotion; or any other surgical procedure or intervention affecting tissue in the oral cavity, anatomic structures in the oral cavity, or alveolar (jaw) bone, or treatment of any acute or chronic oral trauma or condition. According to this aspect of the invention, the systems and methods place a hydrophilic polymer sponge structure in association with tissue or bone affected by the surgical procedure.

Another aspect of the invention provides systems and methods for treating tissue in the oral cavity or alveolar (jaw) bone as a result of an accident that causes injury or trauma to the tissue or bone. According to this aspect of the invention, the systems and methods place a hydrophilic polymer sponge structure in association with the treated tissue or bone.

The assemblies, systems and methods that make use of the hydrophilic polymer sponge structure stanch, seal, or stabilize a site of tissue or bone injury, tissue or bone trauma, or tissue or bone surgery. The use of hydrophilic polymer sponge structure can also form an anti-microbial or anti-viral barrier; and/or promote coagulation; and/or release a therapeutic agent; and/or treat a periodontal or bone surface; and/or combinations thereof.

In accordance with all aspects of the invention, the hydrophilic polymer sponge structure desirably includes a chitosan biomaterial which has been densified by compression prior to use to a density of between 0.6 to 0.1 g/cm3.

Other features and advantages of the invention shall be apparent based upon the accompanying description, drawings, and claims.

BRIEF DESCRIPTION OF THE DRAWINGS

FIG. 6 is a partial close-up anatomical view of the mouth of FIG. 2, showing the palate area where gingiva will be harvested for placement in the area shown in FIG. 5.

FIG. 7 is a perspective view of the gingiva removed from the palate area in FIG. 6.

FIG. 8 depicts the material shown in FIG. 6 being placed within the prepped area of FIG. 5.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. THE DENTAL PAD ASSEMBLY AND USES THEREOF

The present invention provides a dental pad assembly 10 (see FIG. 9A) and methods of using the dental pad assembly 10 that can be used in a variety of dental procedures to promote healing and tissue growth associated with these procedures.

The dental pad assembly 10 comprises a tissue dressing matrix 12. The tissue dressing matrix 12 includes a biocompatible material that reacts in the presence of blood, body fluid, or moisture to become a strong adhesive or glue. Desirably, the tissue dressing matrix also possesses other beneficial attributes, for example, anti-bacterial and/or anti-microbial and/or anti-viral characteristics, and/or characteristics that accelerate or otherwise enhance coagulation, soft tissue healing and the body's defensive reaction to injury. The dressing matrix 12 will be described in further detail, below.

Below are two examples of possible dental procedures where the dental assembly 10 can be used to promote healing and minimize post-surgical issues related to the dental procedures.

A. Free Gingival Graft Procedures

FIGS. 2-13 demonstrates a free gingival graft procedure utilizing the dental assembly 10 of the present invention. Free gingival graft procedures are used when there is inadequate gingiva around a tooth. Gingival material from another section of the person's mouth, typically the palate, will be used to supplement the gingiva in the area that has inadequate gingiva.

Figure 1:
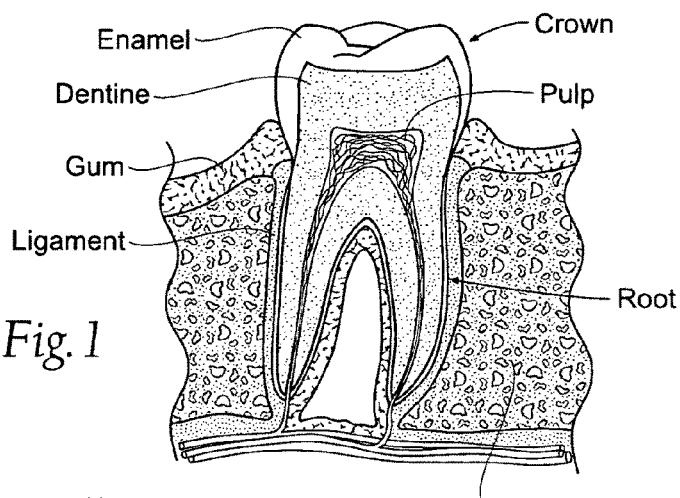
FIG. 1 is an anatomic view of a healthy tooth.
Figure 2:
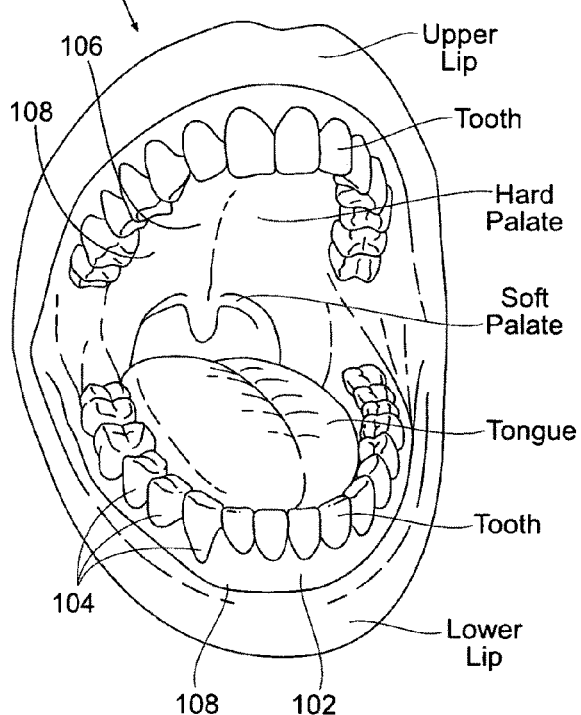
FIG. 2 is an anatomic view of a mouth, including the teeth, gums, and the palate of the mouth.
Figure 3:
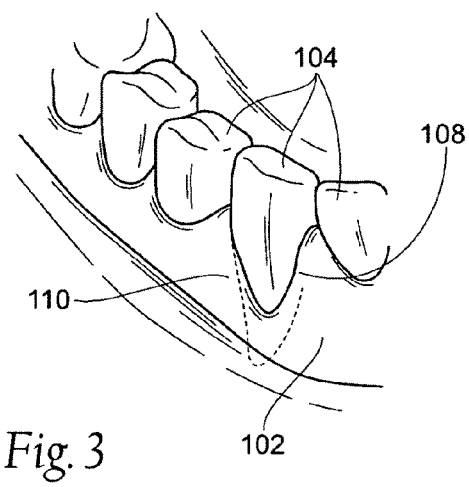
FIG. 3 is a partial close-up anatomical view of the mouth of FIG. 2, showing an area having inadequate gingiva on the crown and root on one tooth within that area.

FIG. 2 shows a person's mouth 100 comprising the gums 102 supporting a plurality of teeth 104. The mouth also has a palate area 106. The gums 102 and the palate area 106 are generally comprised of a gingival material 108. As shown in FIG. 3, the gums 102 have an area 110 that has an inadequate amount of attached gingiva 108 in the area 110. Typically, such an area will be located around the root of the tooth 104, exposing more of the tooth and the root than is desired.

Figure 4:
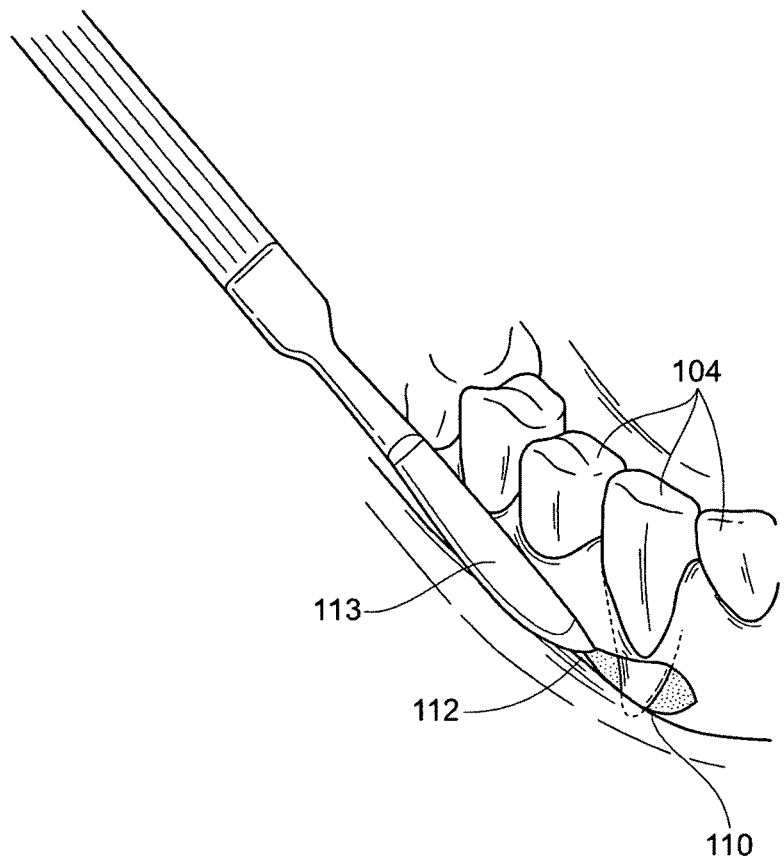
FIG. 4 is an anatomical view of the area of FIG. 3, with the area being prepped for a gingiva transplant.
Figure 5:
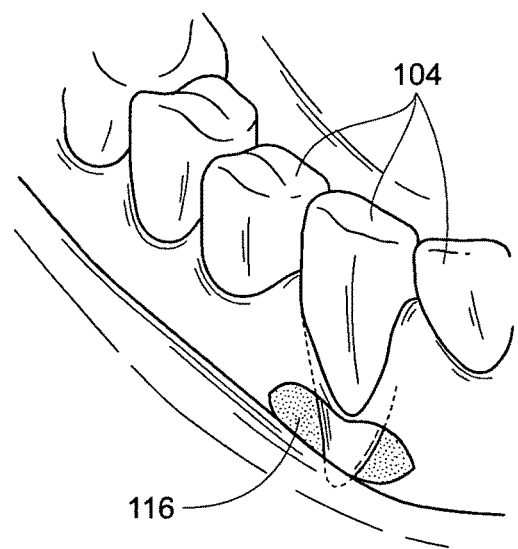
FIG. 5 is an anatomical view of the area of FIG. 4, after the area has been prepped.

FIG. 4 shows the use of a scalpel 113 or other sharpened instrument, to prepare the area 110 for the addition of a gingival graft 114 (see FIG. 7) to the area 110. The outer layer 112 of the area 108 is cut-away to form an opening 116 for insertion of the gingival graft 114, as seen in FIG. 5. The area is preferably cleared away sufficiently to expose the tooth 104, thereby allowing the gingiva to bond directly to the root surface of the tooth 104.

In FIG. 6, the scalpel 113 is used to cut away a small piece of gingival material from the palate area 106 that will be used as the gingival graft 114. The gingival graft 114 is shown in FIG. 7. A pair of forceps 118 can be used to place the graft 114 within the surgical recipient site opening 116, as shown in FIG. 8. Typically, the graft 114 will be held in place with the use of a biologically acceptable glue, periodontal dressing, stent or possibly with sutures.

Figure 9A:
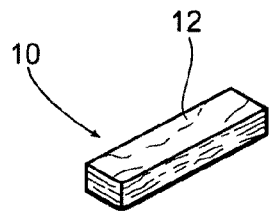
FIG. 9A is a perspective view of the dental pad assembly prior to being finally shaped and configured for placement within the area receiving the gingival transplant.
Figure 9B:
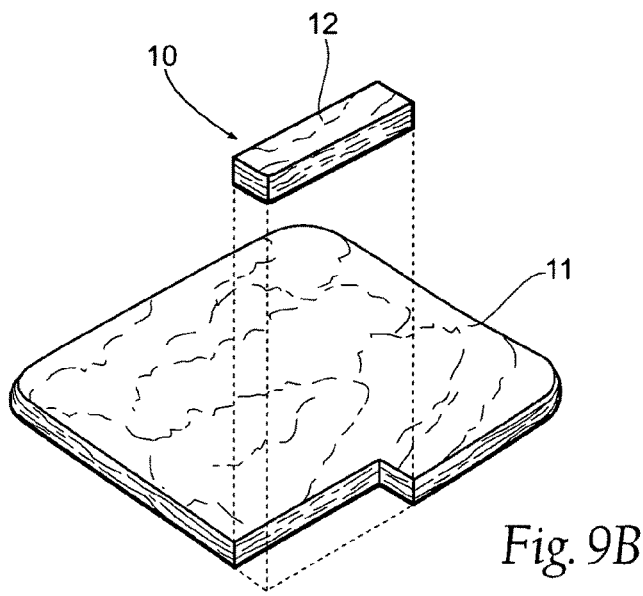
FIG. 9B is a perspective view of the dental pad assembly shown in FIG. 9A cut to a desired size from a larger source pad assembly, prior to being finally shaped and configured for placement within the tooth extraction site.

Once in place, the dental assembly 10 will be placed with the opening 116 over the graft 114. FIG. 9A shows a representative dental pad assembly 10 in its condition prior to use. The size, shape, and configuration of the dental packing pad assembly 10 can vary according to its intended use, which includes taking into account the topolocogy and morphology of the recipient site to be treated and the age/status of the patient (e.g., adult or child). The pad assembly 10 can be rectilinear, elongated, square, round, oval, or a composite or complex combination thereof. Desirably, the shape, size, and configuration of pad assembly 10 can be specially formed and adapted to the topology and morphology of the site of application, by cutting, bending, or molding, either during use or in advance of use. FIG. 9B shows that one or more dental pad assemblies 10 of the same or different desired shapes, sizes, and configurations can be cut from a larger source pad assembly 11.

Figure 10A:
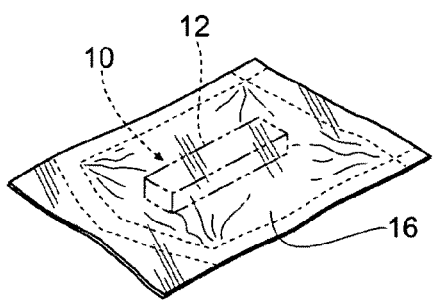
FIGS. 10A and 10B are, respectively, the dental pad assembly shown in FIG. 9A and the source pad assembly shown in FIG. 9B packaged in a sterilized condition within a sealed pouch for use.
Figure 10B:
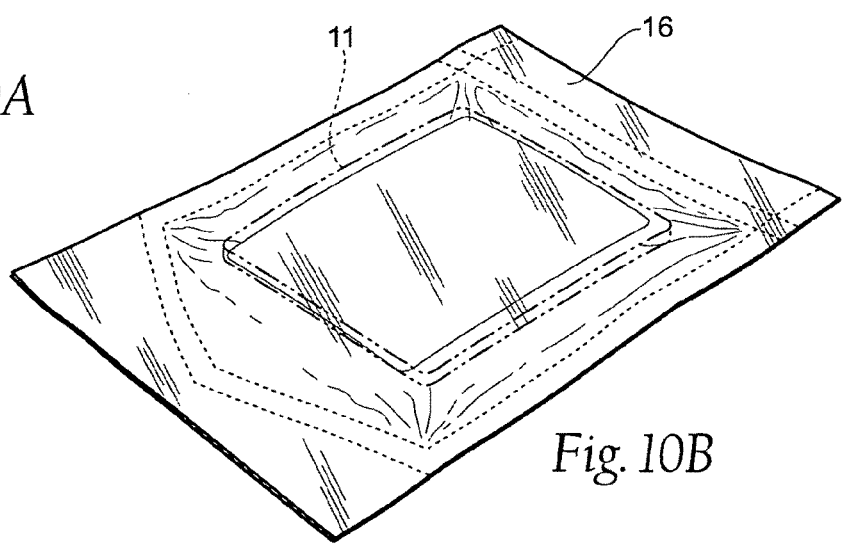
Figure 11:
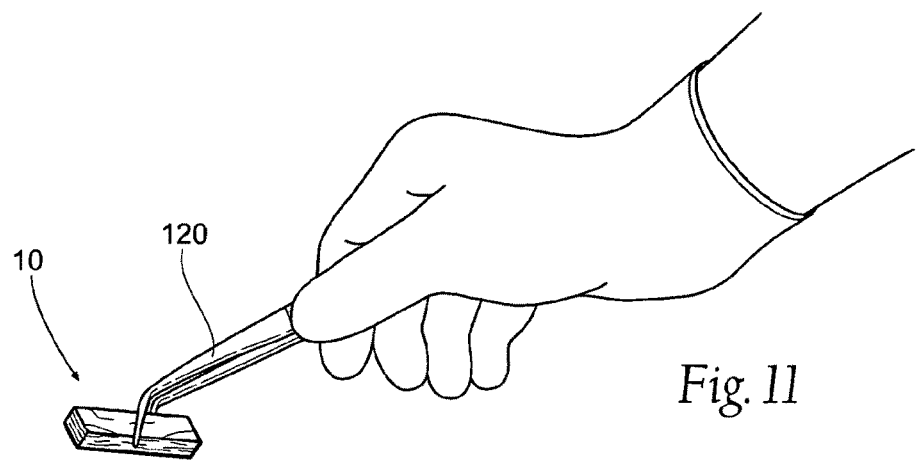
FIG. 11 is a perspective view of the dental pad assembly shown in FIG. 9A, after having been removed from the pouch shown in FIG. 10A in anticipation of use.

As FIGS. 10A and 10B show, the chitosan matrix 12—either in the form of a presized dental pad assembly 10 or as a larger source pad assembly 11 from which presized dental pad assemblies 10 can be cut—is desirably vacuum packaged before use with low moisture content, preferably 5% moisture or less, in an air-tight heat sealed foil-lined pouch 16. The dental pad assembly 10 or source assembly 11 is subsequently terminally sterilized within the pouch 16 by use of gamma irradiation. As FIG. 10B shows, a source pad assembly 11, from which smaller pad assemblies 10 can be cut and sized, can also be vacuum packaged in a sterile condition in a pouch or other delivery device 16 before use. The delivery device 16 could be of a variety of forms, such as form fill and seal containers, capsules, or other containers that will allow for sterile storage of the assembly 10.

The pouch 16 is configured to be peeled opened by the caregiver at the instant of use. The pouch 16 provides peel away access to the tissue dressing pad assembly 10 along one end. The opposing edges of the pouch 16 are grasped and pulled apart to expose the tissue dressing pad assembly 10 for use.

Once removed from the pouch 16 (see FIG. 11), the dental pad assembly 10 is immediately ready to be adhered to the targeted tissue site. It needs no pre-application manipulation to promote adherence. For example, there is no need to peel away a protective material to expose an adhesive surface for use. The adhesive surface forms in situ, because the chitosan matrix 12 itself exhibits strong adhesive properties once in contact with blood, fluid, or moisture. The dental pad assembly 10 need not be applied to the targeted site immediately upon opening the pouch 16.

Figure 12:
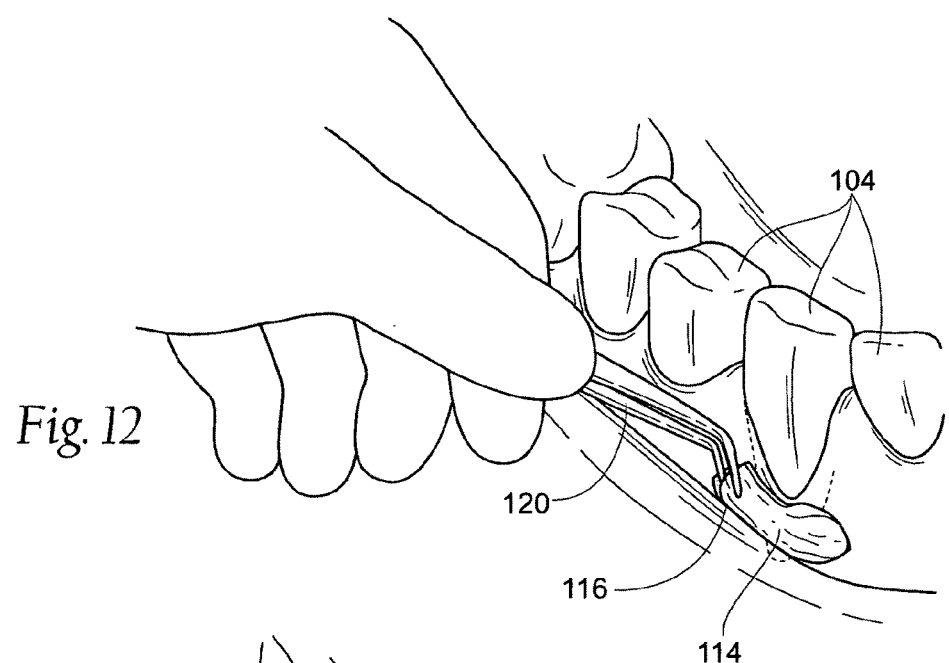
FIG. 12 shows the dental pad assembly of FIG. 11 being placed over the gingival material in FIG. 8.
Figure 13:
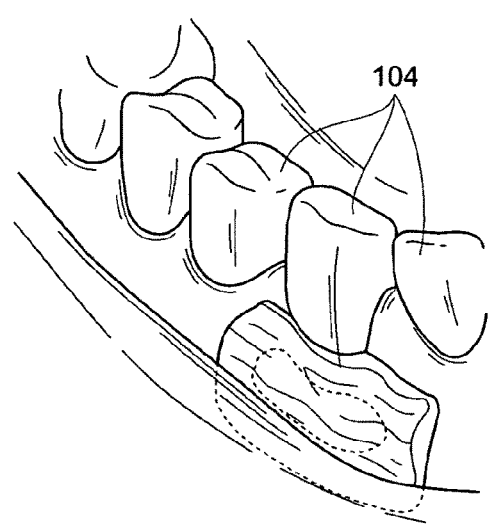
FIG. 13 shows a periodontal dressing being placed over the dental pad assembly and gingival material shown in FIG. 12, to assist in the healing process.

FIG. 12 shows the dental pad assembly 10 being applied over the graft 114. A sterile, dry set of forceps 120 is used to apply the assembly into the opening 116. Because of the make-up of the dental pad assembly 10 and its desire to adhere when near moisture, there is a tendency for the assembly 10 to adhere to the forceps 120 if the forceps 120 are not clean and dry. The dental pad assembly 10 could also be applied with finger pressure, if desired. Because of the properties of the assembly, it is not necessary to use glue or sutures to hold the assembly 10 in place. Similarly, the properties of the assembly promote quick hemostasis of the area 110, thereby minimizing post-operative complications commonly associated with dental procedures. However, as stated, care must be taken so that the assembly 10 does not adhere to a tool or instrument prior to being placed within the opening 116 (see FIG. 8).

After the dental assembly 10 is in place over the graft 114, a periodontal dressing 122 (FIG. 13) can be placed over the opening 116 to further promote healing within the opening 116 and, also, to assist in dissolution of the assembly 10 within the opening 116. Other structures, such as vacuformed stents, can be used to promote dissolution of the assembly 10. The dental assembly 10 can be left in place within the opening 116 during the healing process, or it may be removed after a predetermined period of time, typically about 48 hours or so. As will be discussed in further detail below, the use of the assembly 10 improves efficacy for gingival graft procedures, promotes hemostasis, improves soft tissue healing and reduces secondary problems with the wound sites, such as issues with inflammation, pain, and soft tissue healing.

B. Tooth Extraction Procedures

Figure 14:
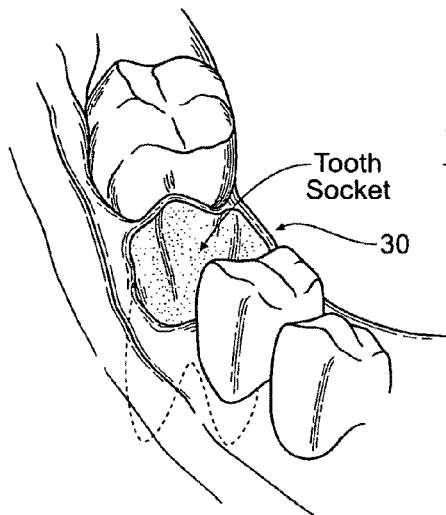
FIG. 14 is an anatomic view of a tooth extraction site in an oral cavity, showing a tooth socket left open by extraction of the tooth.
Figure 15A:
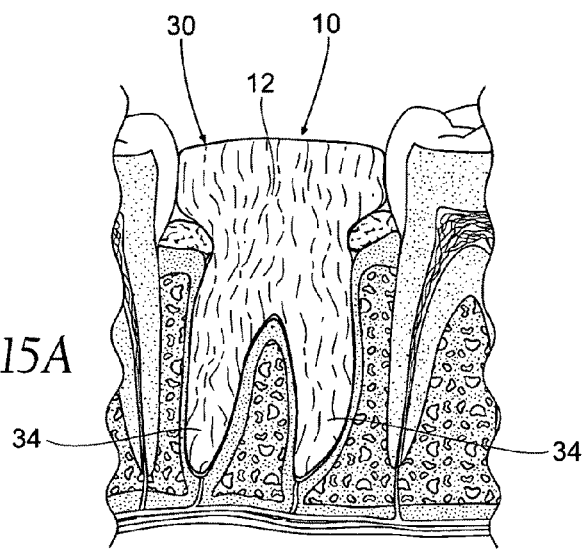
FIGS. 15A and 15B are, respectively, an anatomic lateral perspective view and an anatomic lateral section view of a tooth extraction site into which a dental pad assembly has been placed, the dental pad assembly being capable of adhering to body tissue in the presence of blood, fluid, or moisture to stanch, seal, or stabilize the extraction site during the healing process.
Figure 15B:
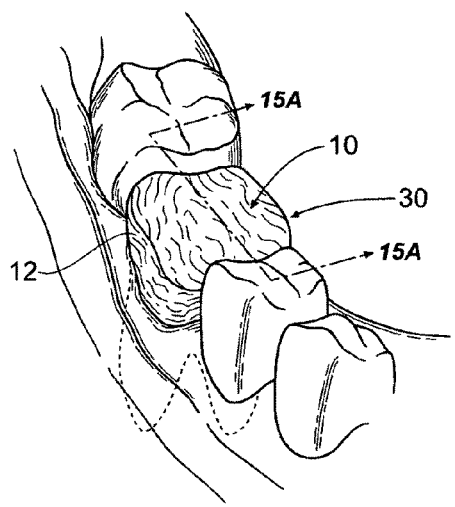
Figure 15C:
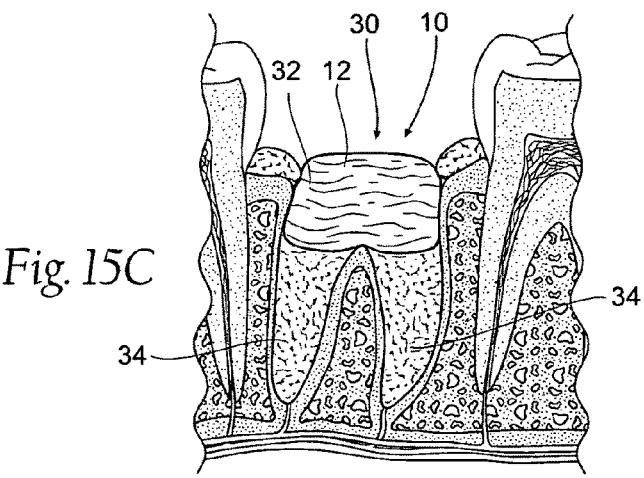
FIG. 15C is an anatomic lateral section view of a tooth extraction site into which a dental pad assembly has been placed, the dental pad assembly forming and providing a barrier within the extraction site capable of adhering to body tissue in the presence of blood, fluid, or moisture to stanch, seal, or stabilize the extraction site during the healing process.

FIG. 14 shows a tooth socket that has been left open following a tooth extraction. FIGS. 15A, 15B, and 15C show the dental pad assembly 10 that embodies features of the invention, after placement into the open tooth socket 30 of the extraction site. The dental assembly 10, as previously described with respect to FIGS. 9A-10B, can be shape, sized, and configured, as necessary. In FIGS. 15A and 15B, the dental pad assembly 10 has been shaped, sized, and configured to be capable of insertion or "packing" into an open tooth socket 30 following extraction of the tooth. The extraction can involve a single tooth (as shown) or multiple teeth.

FIGS. 15A and 15B show the application of the pad assembly 10 within an open tooth socket 30 following an extraction. It should be appreciated that the pad assembly 10 can be shaped, sized, and configured in various ways depending upon the topology and morphology of the tissue site intended to be treated in the oral cavity or surrounding anatomic structures. The targeted treatment site treated can comprise tissue cut or altered or otherwise affected during a dental surgical procedure, e.g., during a tooth extraction. Still, the pad assembly 10 can be shaped, sized, and configured for other types of dental surgical procedures, e.g., endodontic surgery, or periodontal surgery, or orthodontic treatment, or orthognathic surgery, or biopsy, or gingival surgery (discussed above), osseous surgery, or scaling or root planning, or periodontal maintenance, or complete maxillary or mandibular denture, or complete or partial denture adjustment, or denture rebase or reline, or soft tissue surgical extraction, or bony surgical extraction, or installation of an occlusal orthotic device or occlusal guard or occlusal adjustment, or oral surgery involving jaw repair, or bone growth or bone growth promotion, or any acute or chronic trauma, or any other surgical procedure or intervention affecting tissue in the oral cavity, anatomic structures in the oral cavity, or alveolar (jaw) bone. The need for applying the dental pad assembly 10 can also arise as a result of an accident that causes injury or trauma to tissue or structures in the oral cavity or alveolar (jaw) bone.

FIG. 15C is an alternate view to that shown in FIG. 15A demonstrating the dental pad assembly 10 being inserted into the open tooth socket 30. The dental pad assembly 10 is generally shaped, sized and configured to fit into the upper area 32 of the tooth socket 30, with dental pad assembly 10 generally not extending into the roots 34. Because of the complex shape of the extraction socket 30 and the individual roots 34, it is not practical that the dental pad assembly 10 will be able to be shaped and configured to fit within the entire socket 30. As such, the dental pad assembly 10 will be positioned within the upper area 32 and forming a barrier for blood and fluids to interact with. The blood and fluids will fill in the roots 34 up to the positioned assembly 10, which will than initiate clotting of the blood and fluids, which leads to increased and expedient soft tissue healing and potentially leading to improved bone mass, since the clot formed between the blood and dental assembly 10 retains a relatively large surface area.

It should be understood that either arrangement of FIG. 15A or FIG. 15C are possible under the scope of the present invention, as well as other arrangements of the dental pad assembly 10. Provided that the assembly 10 will provided therapeutic and hemostatic properties, the positioning or arrangement would fall within the scope of the present invention.

Figure 16:
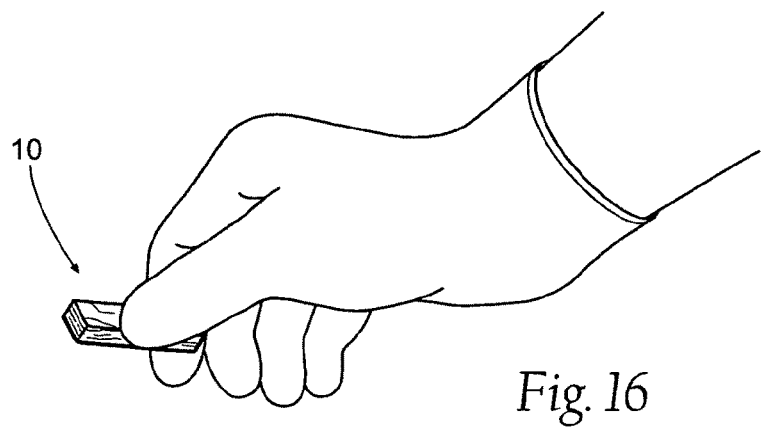
FIG. 16 is a perspective view of the dental pad assembly shown in FIG. 9A, after having been removed from the pouch shown in FIG. 10A in anticipation of use and prior to being finally shaped and configured for placement within the extraction site.

FIG. 16 shows an individual dental pad assembly 10 for insertion within the open tooth socket. As previously described with respect to FIGS. 9A-10B, the dental pad assembly 10 can be cut and formed from the source assembly 11 as desired. Alternatively, the dental assembly 10 could be packaged and designed individually in a shape that would resemble the particular oral cavity, lesion, or opening that the assembly 10 is to be used in connection with.

Figure 17:
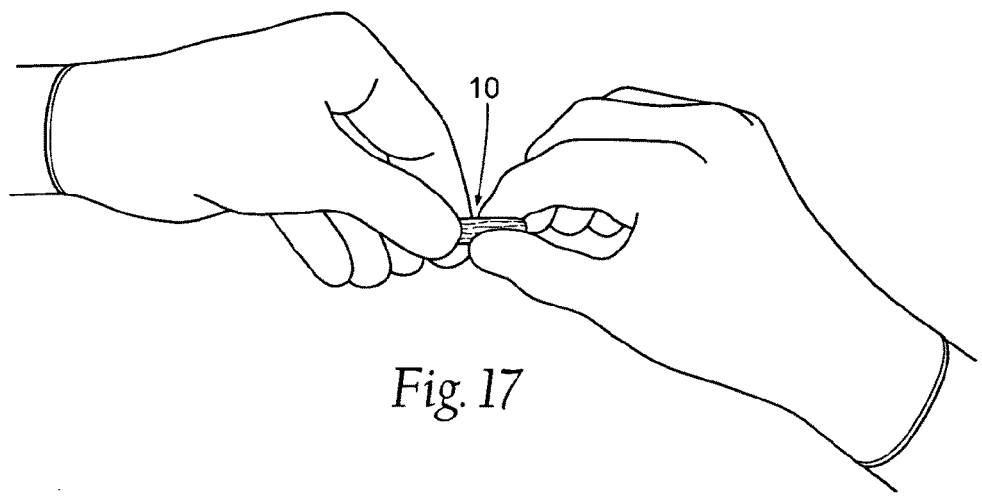
FIG. 17 is a perspective view of the dental pad assembly shown in FIG. 16 being held and manipulated by folding or bending prior to use to conform to the topology of a targeted tissue site.

As FIG. 17 shows, the dental pad assembly 10 can be shaped and adapted on site to conform to the topology and morphology of the targeted site, which in the illustrated embodiment is a tooth socket following a tooth extraction. The practitioner can obtain a dental impression reflecting the size and spacing of teeth in the area of the extraction, and use the impression to aid in sizing and shaping the pad assembly 10. The dental pad assembly 10 can be deliberately molded into many configurations, e.g., into a cylinder or a cup-shape, to best conform to the particular topology and morphology of the treatment site. As previously described (see FIG. 9B), one or more pad assemblies 10 can be cut and shaped on site from a larger source assembly 11.

Figure 18:
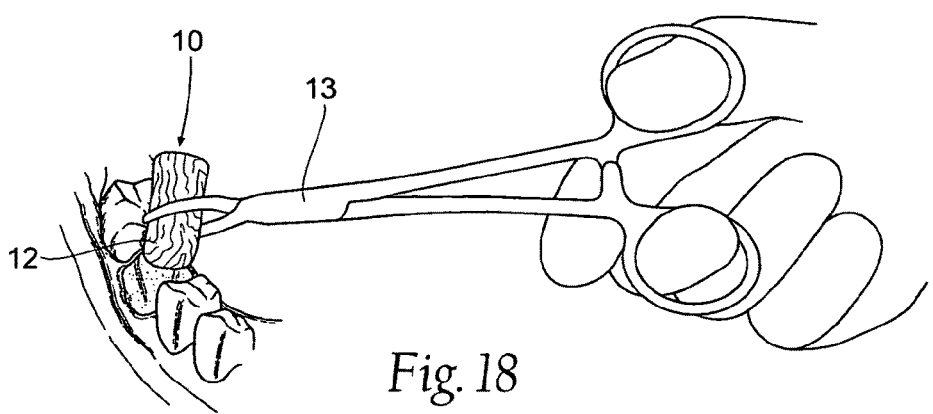
FIG. 18 is a perspective view of the dental pad assembly being placed within the targeted extraction site.

FIG. 17 shows the chitosan dental pad assembly 10 being positioned in association with a targeted treatment site, which in the illustrated embodiment is a tooth extraction site. As FIG. 18 shows, the dental pad assembly 10 is placed and pressed into the tooth socket (e.g., by hand or using a forceps 13) with the chitosan matrix 12 directed against the site of active bleeding or where adherence is otherwise desired, so that direct pressure can be applied to the bleeding tissue (see FIG. 19 also). As FIG. 15A shows, the pad assembly 10 is shaped, sized, and configured so that a portion of the pad assembly 10 extends from the socket between the remaining teeth and is held in place by the opposing teeth. Desirably, once applied to a site where adherence is desired, the caregiver should avoid repositioning the dental pad assembly 10. Also, as shown in FIG. 15C, the dental pad assembly 10 can be shaped and trimmed to fit within the extraction socket 32, with the dental pad assembly 10 generally being held in place with friction with the surrounding soft tissue and bone until a clot is formed between the blood and the pad assembly 10, which will hold the pad assembly 10 in place.

Figure 19:
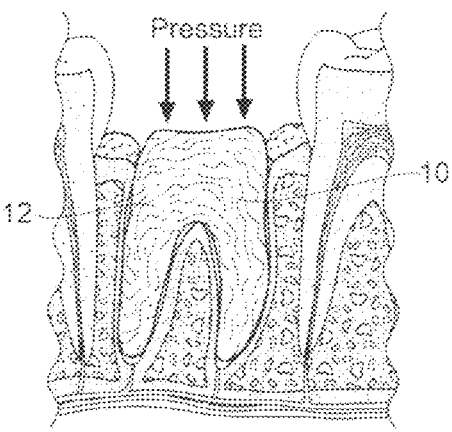
FIG. 19 is a side section view of the dental pad assembly, after placement within the targeted extraction site, with pressure being temporarily applied to adhere the pad assembly to the site and stanch bleeding.

Desirably, as FIG. 19 shows, firm pressure is applied about two minutes, to allow the natural adhesive activity of the chitosan matrix 12 to develop. In this way, virtually all of the compressive force retained by the opposing teeth facing the extraction site is transmitted through substantially all of the mass of the pad assembly 10. The adhesive strength of the chitosan matrix 12 will increase with duration of applied pressure, up to about five minutes. Pressure applied evenly across the dental pad assembly 10 during this time (as shown by arrows in FIG. 19) will provide more uniform adhesion and wound sealing. Pressure can be applied with the aid of a gauze compress, if desired. The patient can also apply and maintain pressure by biting down.

The site treated by the pad assembly 10 can involve arterial and/or venous bleeding caused by a surgical instrument or trauma or injury; or by the placement during surgery or a dental procedure of a wire, staples, fasteners, or sutures; or caused accidentally by a laceration, or a wound, or a puncture, or a burn, or a bone fracture, or crush injury. The dental pad assembly 10 can be sized and configured to be inserted or placed in association with any type of tissue disruption, trauma, or injury in the oral cavity or on or in proximity to adjacent anatomic structures.

Regardless of the cause, the properties of the matrix 12 of the pad assembly 10 serve to moderate bleeding, fluid seepage or weeping, or other forms of fluid loss, while also promoting healing.

Due to the properties of the matrix 12, the dental pad assembly 10 can also desirably form an anti-bacterial and/or anti-microbial and/or anti-viral protective barrier at or surrounding the tissue treatment site in an oral cavity.

Due to the special properties of the chitosan matrix 12, the dental pad assembly 10 also may be indicated for use with individuals undergoing dental procedures or suffering tissue trauma in the oral cavity, who have various types of bleeding or coagulation disorders, such as hemophilia, or idiopathic thrombocytopenic purpura (ITP) (which can itself lead to bleeding gums). The presence of the chitosan matrix 12 attracts red blood cell membranes, which fuse to chitosan matrix 12 upon contact. A clot can be formed very quickly and does not need the clotting proteins that are normally required for coagulation. Even in individuals without bleeding or coagulation disorders, the presence of the chitosan matrix 12 can accelerate the clotting process independent of the clotting cascade. For this reason, the matrix 12 can be used with no loss of efficacy in conjunction with anticoagulants/blood thinners such as heparin, clopidogrel bisulfate (PLAVIX®), acetylsalicylic acid, dipyridamole, etc.

The dental pad assembly 10, when used during or after a dental procedure or accidental trauma in the oral cavity, can also provide a topically applied platform for the delivery of one or more therapeutic agents into the blood stream in a controlled release fashion. The therapeutic agents can be incorporated into the hydrophilic polymer sponge structure, e.g., either before or after the freezing step, and before the drying and densification steps, as will be described later. Examples of therapeutic agents that can be incorporated into a hydrophilic polymer sponge structure (e.g., the chitosan matrix 12) include, but are not limited to, drugs or medications, stem cells, antibodies, anti-microbials, anti-virals, collagens, genes, DNA, and other therapeutic agents; hemostatic agents like fibrin; growth factors; Bone Morphogenic Protein (BMP); peptides; STAMPS; DNA vaccines and similar compounds.

The beneficial properties of chitosan matrix 12 includes adherence to mucosal surfaces within the body, such as those lining the mouth. This feature makes possible the incorporation of the chitosan matrix 12 in systems and devices directed to treating mucosal surfaces where the adhesive sealing characteristics, and/or accelerated clotting attributes, and/or anti-bacterial/anti-viral features of the chitosan matrix 12, as described, provide advantages. Such systems and methods can include the gum repairs and sealing about sutures placed in the oral cavity.

The chitosan matrix 12 of the pad assembly 10 does more than soak up blood as a clot forms within the socket. The adhesive strength of the chitosan matrix 12 causes it to adhere to tissue within the socket, so that mechanical properties of the pad assembly 10 apply direct pressure. Further, the presence of the chitosan matrix 12 attracts red blood cell membranes, which fuse to chitosan matrix 12 upon contact. A clot can be formed very quickly and does not depend solely upon the clotting proteins that are normally required for coagulation. The presence of the chitosan matrix 12 can accelerate the clotting process independent of the clotting cascade. Also further, the presence of the chitosan matrix 12 can provide an anti-bacterial and/or anti-microbial and/or anti-viral protective effect. Hemostasis occurs in about one minute using the chitosan matrix 12 in dental applications, compared to about seven minutes using conventional cotton packs and rolled or folded gauze pads.

The dental pad assembly 10 can be torn or cut on site to match the size of the extraction site, as previously described. Smaller, patch pieces of a pad assembly 10 can also be cut to size on site, and fitted and adhered in other pieces already placed to best approximate the topology and morphology of the treatment site.

Desirably, the dental pad assembly 10 is allowed to reside within the socket during the healing process for the prevention of pain and the promotion of rapid healing. The presence of chitosan matrix 12 within the socket provides an environment conducive to retention of the clot (thereby avoiding dry socket) as well as the general healing process, during which new bone and gum tissue grow into the gap left by the extraction. The physical presence of the chitosan matrix 12—which, desirably, is purposely densified during its manufacture to resist dissolution—acts as a bone covering obtundant and physiologic scaffolding for the conduction of normal alveolar bone heal process of fibroblast ingrowth, blood vessel formation, and reossification of the extraction site. The enhanced physical properties of the densified chitosan matrix 12 further enhanced by the adhesive strength of the chitosan matrix 12, its self-promotion of coagulation, and its anti-bacterial/anti-microbial/anti-viral properties.

As previously described, the pad assembly 10 can incorporate a medication or physiologic or pharmacologic agent that acts locally or systemically in the body, e.g., enzymes, organic catalysts, ribozymes, organometallics, proteins, glycoproteins, peptides, polyamino acids, antibodies, nucleic acids, steroidal molecules, antibiotics, antimycotics, cytokines, growth factors for tissue and/or bone, carbohydrates, oleophobics, lipids, extracellular matrix and/or individual components, mammalian cells, stem cells, genetically engineered cells, pharmaceuticals, peptides, STAMPS, DNA vaccines and therapeutics. The pad assembly 10 provides a physically stable, biocompatible, and non-cytotoxic environment promoting a rapid and pain-free recovery period.

Desirably, the pad assembly 10 is removed and, if indicated, replaced within forty-eight hours of application. The pad assembly 10 can be peeled away and will generally separate from the treatment site in a single, intact dressing. In some cases, residual chitosan gel may remain, and this can be removed using a saline or water wash, with gentle abrasion using a gauze dressing or irrigation syringe, if required.

Chitosan is biodegradable within the body and is broken down into glucosamine, a benign substance. Still, efforts should be made to remove all portions of chitosan from the wound at the time of definitive repair.

C. The Tissue Dressing Matrix

The tissue dressing matrix 12 desirably comprises a hydrophilic polymer form, such as a polyacrylate, an alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may be of amylase, amylopectin and a combination of amylopectin and amylase.

In a preferred embodiment, the biocompatible material of the matrix 12 comprises a non-mammalian material, which is most preferably poly [$\beta$-(1→4)-2-amino-2-deoxy-D-glucopyranose, which is more commonly referred to as chitosan.

Due to the special properties of the chitosan matrix 12, the dental pad assembly 10 is capable of adhering to tissue within the socket in the presence of blood, or body fluids, or moisture. The presence of the dental pad assembly 10 stanches, seals, and/or stabilizes the extraction site, while establishing conditions conducive to the formation and maintenance of a blood clot at the wound during the healing process.

The tissue dressing matrix 12 is preferably formed from a low modulus hydrophilic polymer matrix, i.e., an inherently "uncompressed" tissue dressing matrix 12, which has been densified by a subsequent densification process, which will be described later. As previously described, the tissue dressing matrix 12 may comprise a hydrophilic polymer form, which, in a preferred form, comprises a non-mammalian material poly [$\beta$-(1→4)-2-amino-2-deoxy-D-glucopyranose, which is more commonly referred to as chitosan.

The chitosan selected for the matrix 12 preferably has a weight average molecular weight of at least about 100 kDa, and more preferably, of at least about 150 kDa. Most preferably, the chitosan has a weight average molecular weight of at least about 300 kDa.

In forming the matrix 12, the chitosan is desirably placed into solution with an acid, such as glutamic acid, lactic acid, formic acid, hydrochloric acid and/or acetic acid. Among these, hydrochloric acid and acetic acid are most preferred, because chitosan acetate salt and chitosan chloride salt resist dissolution in blood whereas chitosan lactate salt and chitosan glutamate salt do not. Larger molecular weight (Mw) anions disrupt the para-crystalline structure of the chitosan salt, causing a plasticization effect in the structure (enhanced flexibility). Undesirably, they also provide for rapid dissolution of these larger Mw anion salts in blood.

One preferred form of the matrix 12 comprises an "uncompressed" chitosan acetate matrix 12 of density less than 0.035 $g/cm^3$ that has been formed by freezing and lyophilizing a chitosan acetate solution, which is then densified by compression to a density of from 0.6 to 0.25 $g/cm^3$, with a most preferred density of about 0.20 $g/cm^3$. This chitosan matrix 12 can also be characterized as a compressed, hydrophilic sponge structure. The densified chitosan matrix 12 exhibits all of the above-described characteristics deemed to be desirable. It also possesses certain structural and mechanical benefits that lend robustness and longevity to the matrix during use, as will be described in greater detail later.

The chitosan matrix 12 presents a robust, permeable, high specific surface area, positively charged surface. The positively charged surface creates a highly reactive surface for red blood cell and platelet interaction. Red blood cell membranes are negatively charged, and they are attracted to the chitosan matrix 12. The cellular membranes fuse to chitosan matrix 12 upon contact. A clot can be formed very quickly, circumventing immediate need for clotting proteins that are normally required for hemostasis. For this reason, the chitosan matrix 12 is effective for both normal as well as anti-coagulated individuals, and as well as persons having a coagulation disorder like hemophilia. The chitosan matrix 12 also binds bacteria, endotoxins, and microbes, and can kill bacteria, microbes, and/or viral agents on contact.

Further details of the structure, composition, manufacture, and other technical features of the chitosan matrix 12 will be described later.

D. Experimental Results

Example 1

Free Gingival Procedures

Example 1 demonstrates the efficacy of a dental pad assembly as described above in free gingival procedures. The dressing assembly 10 was assessed for effectiveness of managing post-surgical sequelae, ease of handling; and comparing the dressing assembly 10 performance in oral surgery and periodontal surgery procedures. The primary objectives was to evaluate the effectiveness of using a 1"×3" dressing pad assembly 10 for hemostasis and soft tissue healing response of maxillary donor sites during and after periodontal free gingival graft surgical procedures. The dressing pad assemblies 10 can be torn or cut to a desired size, as described, above, with respect to the description of the use of a dental pad assembly, or could be manufactured for the desired size.

Patients were used who required free gingival grafts or connective tissue grafts. The patients were required to return for a 7-day post-operative visit and had a willingness and availability to provide informed consent. Patient that were excluded from the study included patients that had scheduled dental or surgical procedure other than noted in inclusion criteria; required procedures involving primary closure of the dressing assembly 10 within the surgical wound; and inability to provide informed consent. The study was reviewed by an Investigational Review Board prior to the study, and was conducted in accordance with the Helsinki Declaration of 1975, as revised in 2000.

The following potentially confounding variables of individual patients were considered if they were significant: prothrombin or other laboratory tests in patients taking blood thinning medication; age and gender; hypertension (defined as a systolic blood pressure greater than 140 mm mercury); patients who smoked or used tobacco products; patients taking birth control pills; and patients taking bisphosphonate therapies.

Example 1 was conducted as a 2-site, externally controlled study involving one or more periodontal surgery sites per patient. During each surgical procedure, the dressing assembly 10 was cut to size (based on each subject's individual wound size) within the sterile field using sterile scissors, and placed on the oral surgical wound without the use of sutures. The custom trimmed dressing assembly 10 was initially stabilized with either finger pressure or by using a clean dry surgical instrument so that the dressing did not adhere to the instrument. It should be noted that a clean dry surgical instrument is needed, so that the dressing assembly 10 will not adhere to the instrument when being inserted. The time to hemostasis was noted.

Figure 20:
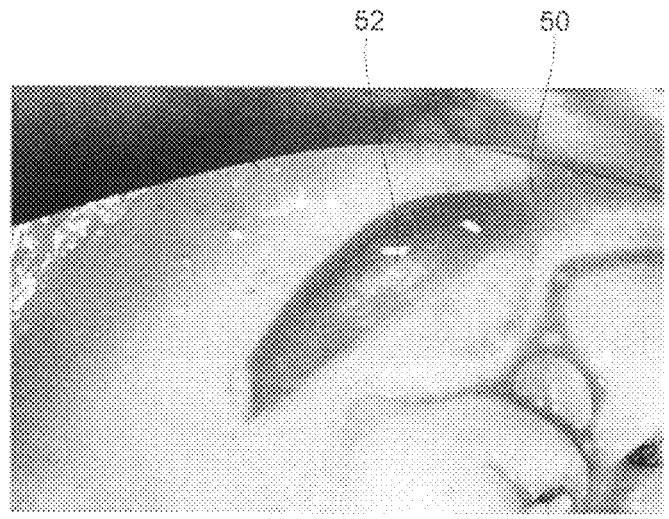
FIG. 20 is a photograph of a maxillary donor site demonstrated in FIG. 6 showing the surgical site after gingiva has been harvested.
Figure 21:
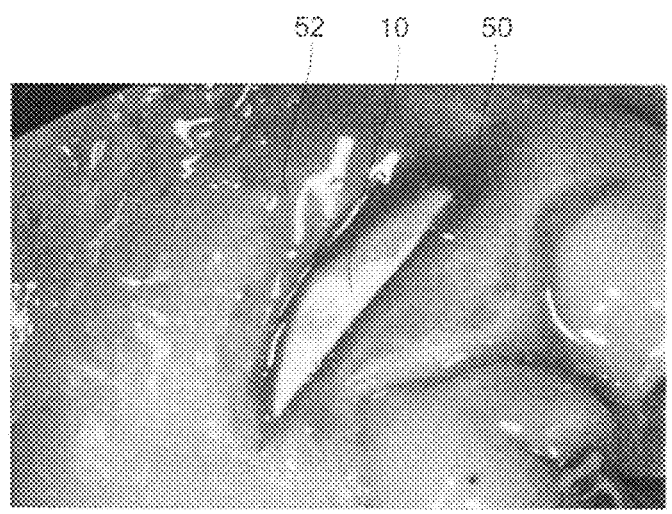
FIG. 21 is a photograph of a maxillary site shown in FIG. 20, with the dental pad assembly of the present invention being inserted into the incision of the mandibular site.

FIG. 20 is a photograph of a dental area 50 with a wound site 52. Palatal gingival was harvested from the wound site 52, i.e. the maxillary palate donor site. Once the wound site 52 was properly cleaned and prepped, a dressing assembly 10 was shaped to fit within the wound site 52, as shown in FIG. 21. As stated above, the dressing assembly 10 was not used with all of the patients.

Figure 22:
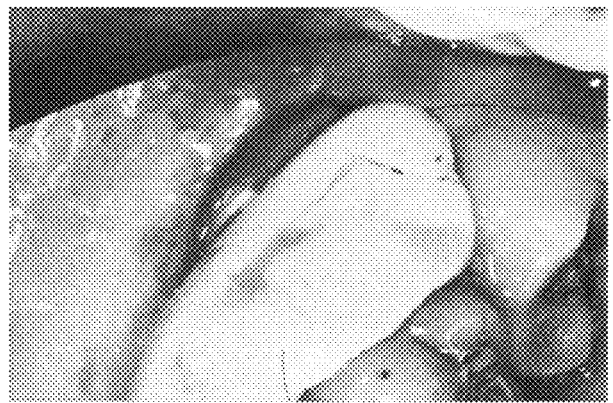
FIG. 22 is a photograph of the maxillary site of FIG. 20 with a periodontal dressing being placed over the incision.

The wound was either covered with a standard periodontal dressing 54, as shown in FIG. 22, covered with a clear surgical vacuformed stent, or covered with a clear surgical vacuformed stent that had four number 6 round bur holes placed over the wound site to facilitate dissolution of the dressing assembly 10 during the first two or three days after surgery. Control patients followed the same postoperative standard of care protocols without the use of the dressing assembly 10.

If a periodontal dressing was used, it was placed in such a manner to assure that the dressing assembly 10 was exposed to oral fluids and remained in place until the 7-day postoperative visit. Those patients using a vented or non-vented surgical stent were instructed to remove the stent 48 hours after surgery for cleaning, and then replace the stent to protect the surgical wound until the 7-day post operative appointment.

Surgical wounds were evaluated for time to hemostasis, immediate soft tissue response, post-surgery inflammation, pain, and 7-day healing response. If hemostasis was not achieved in 60 seconds, the surgeon observed the surgical site at designated intervals until hemostasis was achieved. The dressing assembly 10 was allowed to remain in place without sutures for a maximum of 7-days post surgery. If available, the number of days that a dressing remained on the wound (based on dressing exposure and tongue activity) was noted. Any remaining residual dressing material was removed by water irrigation at the 7-day post surgery follow-up visit. At the conclusion of the study, ease of handling and use by the practitioner during the surgical procedure was noted.

Figure 23:
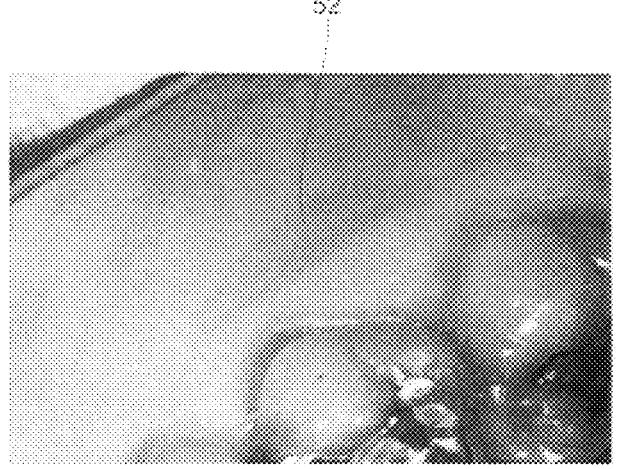
FIG. 23 is a photograph of the maxillary site of FIG. 20 one week after insertion of the dental pad assembly of FIG. 21 and being covered with the periodontal dressing of FIG. 22. The surgical donor site demonstrates advanced healing and complete closure of the surgical wound.
Figure 24:
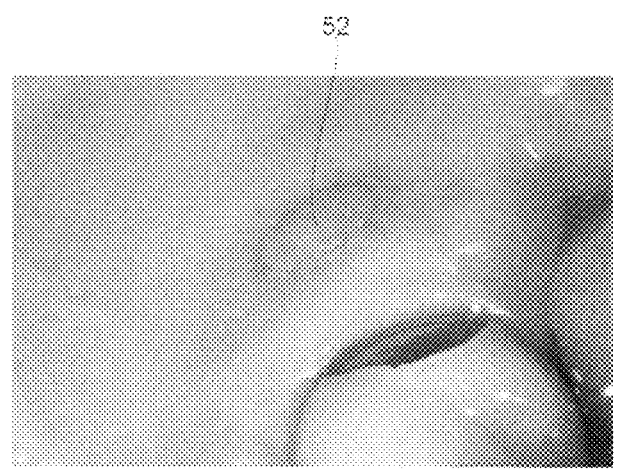
FIG. 24 is a photograph of the mandibular site of FIG. 10 after one week of being covered with the periodontal dressing of FIG. 22, without the insertion of the dental pad assembly of FIG. 21. The surgical donor site demonstrates normal healing with incomplete closure of the surgical wound and a large central core of inflammatory tissue.

Digital pictures were taken immediately following the surgical procedure for all control and surgical sites, and again at the 7-day post-operative visit. FIGS. 23 and 24 provide photographs that compare wound sites 52 after the 7-day period, with the use of a dressing assembly 10 shown in FIG. 23 and treatment without a dressing assembly 10 shown in FIG. 24. The photograph in FIG. 23 (use of the dressing assembly) shows improved healing progress with complete wound closure compared to that shown in FIG. 24B (no dressing assembly used) of the control with incomplete wound closure and large central core or healing inflammatory tissue.

After all post-surgical follow-up visits were completed and photographs taken, an independent panel of nine (9) specially trained periodontists and general dentists evaluated the surgical site photographs for healing. The panelists were blinded to the treatment protocol used and whether the patient was a study subject or control. Three criteria were evaluated: pain, inflammation, and progression of healing. Wounds were graded from 0 (poor) to 5 (normal) to 10 (best). A pictorial evaluation guide was provided to each panelist to minimize evaluation variability.

Patient demographics are summarized in Table 1. 33 females and 15 males between the ages of 8 to 76 years of age (median age 49.5) were chosen for the study. Eight patients discontinued aspirin therapy 5 days prior to the surgery. One patient was under aspirin therapy at the time of the surgery. Twenty-five patients were treated using the dressing assembly 10 dressing covered with a periodontal dressing (with 9 controls); 7 were treated using the dressing assembly 10 and a solid stent (with 6 controls), and 4 were treated using the dressing assembly 10 dressing and a perforated stent (with no controls). One patient had two procedures.

TABLE 1

Patient Demographics

| Parameter | Control (No Dressing Assembly) (N = 15) | Dressing assembly (N = 33) | TOTAL (N = 48) |
|---|---|---|---|
| Time to Hemostasis (minutes) All Treatment Groups Combined | | | |
| No. of Patients | 15 | 33 | 48 |
| Mean (SD) | 40.7 (16.73) | 41.9 (20.68) | 41.5 (19.36) |
| Median | 44.0 | 50.0 | 49.5 |
| (Minimum, Maximum) | (14.0, 62.0) | (8.0, 76.0) | (8.0, 76.0) |
| Periodontal Dressing | | | |
| No. of Patients | 9 | 25 | 34 |
| Mean (SD) | 41.8 (17.34) | 43.5 (21.32) | 43.0 (20.10) |
| Median | 44.0 | 52.0 | 51.0 |
| (Minimum, Maximum) | (14.0, 62.0) | (8.0, 76.0) | (8.0, 76.0) |
| Solid Stent | | | |
| No. of Patients | 6 | 5 | 11 |
| Mean (SD) | 39.0 (17.23) | 39.6 (21.00) | 39.3 (18.02) |
| Median | 44.0 | 45.0 | 45.0 |
| (Minimum, Maximum) | (18.0, 59.0) | (17.0, 65.0) | (17.0, 65.0) |
| Perforated Stent | | | |
| No. of Patients | 0 | 3 | 3 |
| Mean (SD) | N/A | 32.7 (18.18) | 32.7 (18.18) |

TABLE 1-continued

Patient Demographics

| Parameter | Control (No Dressing Assembly) (N = 15) | Dressing assembly (N = 33) | TOTAL (N = 48) |
|---|---|---|---|
| Median | N/A | 27.0 | 27.0 |
| (Minimum, Maximum) | N/A | (18.0, 53.0) | (18.0, 53.0) |
| Gender [n %] All Treatment Groups Combined | | | |
| Male | 4 (26.7%) | 10 (30.3%) | 14 (29.2%) |
| Female | 11 (73.3%) | 23 (69.7%) | 34 (70.8%) |
| Periodontal Dressing | | | |
| Male | 2 (13.3%) | 9 (27.3%) | 11 (22.9%) |
| Female | 7 (46.7%) | 16 (48.5%) | 23 (47.9%) |
| Solid Stent | | | |
| Male | 2 (13.3%) | 1 (3.0%) | 3 (6.3%) |
| Female | 4 (26.7%) | 4 (12.1%) | 8 (16.7%) |
| Perforated Stent | | | |
| Male | 0 (0%) | 0 (0%) | 0 (0%) |
| Female | 0 (0%) | 3 (9.1%) | 3 (6.3%) |

Results

Hemostasis:

The dressing assembly 10 had a 1.5 minute average hemostasis time, which was a statistically significantly faster time than the control for both periodontal dressing and surgical stents. The dressing assembly 10 hemostasis time (p=0.0147) would have been even shorter except for the inclusion of a 9.4 minute dressing assembly 10 hemostasis time for one patient who suffered a possible bleeding event involving the greater palatine artery that was controlled using the dressing assembly 10 without suturing but had prolonged minor oozing. Control bleeding time averaged 3.2 minutes.

TABLE 2

Time to Hemostasis

| Parameter | Control (No Dressing Assembly) (N = 14) | Dressing assembly (N = 33) | TOTAL (N = 47) |
|---|---|---|---|
| Time to Hemostasis (minutes) All Treatment Groups Combined | | | |
| No. of Patients | 14 | 33 | 47 (p = 0.0147) |
| Mean (SD) | 3.3 (1.66) | 2.0 (1.74) | 2.4 (1.81) |
| Median | 3.2 | 1.5 | 2.3 |
| (Minimum, Maximum) | (0.4, 7.0) | (0.0, 9.4) | (0.0, 9.4) |
| Periodontal Dressing | | | |
| No. of Patients | 8 | 25 | 33 |
| Mean (SD) | 2.6 (1.05) | 1.9 (1.84) | 2.1 (1.69) |
| Median | 3.2 | 1.3 | 2.2 |
| (Minimum, Maximum) | (0.4, 3.4) | (0.3, 9.4) | (0.3, 9.4) |
| Solid Stent | | | |
| No. of Patients | 6 | 5 | 11 |
| Mean (SD) | 4.3 (1.94) | 2.3 (1.82) | 3.4 (2.06) |
| Median | 4.0 | 2.5 | 2.5 |
| (Minimum, Maximum) | (2.0, 7.0) | (0.0, 5.0) | (0.0, 7.0) |
| Perforated Stent | | | |
| No. of Patients | 0 | 3 | 3 |
| Mean (SD) | N/A | 2.0 (1.00) | 2.0 (1.00) |
| Median | N/A | 2.0 | 2.0 |
| (Minimum, Maximum) | N/A | (1.0, 3.0) | (1.0, 3.0) |

Inflammation:

Inflammation scores were reduced (p=0.1120) in patients treated with the dressing assembly 10 compared to control. Inflammation scores for those patients treated with dressing assembly 10 and periodontal dressing or perforated stents had minimal, if any, post operative inflammation.

TABLE 3

Inflammation Score By Treatment Group

| Parameter | Control (No dressing assembly) (N = 15) | Dressing Assembly (N = 33) | TOTAL (N = 48) | p-Value* |
|---|---|---|---|---|
| Inflammation Score All Treatment Groups Combined | | | | 0.1120 |
| No. of Patients | 15 | 33 | 48 | |
| Mean (SD) | 0.8 (0.68) | 0.5 (0.62) | 0.6 (0.65) | |
| Median | 1.0 | 0.0 | 0.5 | |
| (Minimum, Maximum) | (0.0, 2.0) | (0.0, 2.0) | (0.0, 2.0) | |
| Periodontal Dressing | | | | 0.3139 |
| No. of Patients | 9 | 25 | 34 | |
| Mean (SD) | 0.6 (0.53) | 0.4 (0.49) | 0.4 (0.50) | |
| Median | 1.0 | 0.0 | 0.0 | |
| (Minimum, Maximum) | (0.0, 1.0) | (0.0, 1.0) | (0.0, 1.0) | |
| Solid & Perforated Stent | | | | 0.4912 |
| No. of Patients | 6 | 8 | 14 | |
| Mean (SD) | 1.2 (0.75) | 0.9 (0.83) | 1.0 (0.78) | |
| Median | 1.0 | 1.0 | 1.0 | |
| (Minimum, Maximum) | (0.0, 2.0) | (0.0, 2.0) | (0.0, 2.0) | |
| Solid Stent | | | | |
| No. of Patients | 6 | 5 | 11 | |
| Mean (SD) | 1.2 (0.75) | 0.6 (0.89) | 0.9 (0.83) | |
| Median | 1.0 | 0.0 | 1.0 | |
| (Minimum, Maximum) | (0.0, 2.0) | (0.0, 2.0) | (0.0, 2.0) | |
| Perforated Stent | | | | |
| No. of Patients | 0 | 3 | 3 | |
| Mean (SD) | N/A | 1.3 (0.58) | 1.3 (0.58) | |
| Median | N/A | 1.0 | 1.0 | |
| (Minimum, Maximum) | N/A | (1.0, 2.0) | (1.0, 2.0) | |

TABLE 4

Inflammation Score dressing assembly 10 Patients

| | Periodontal Dressing (N = 25) | Solid and Perforated Stent (N = 8) | TOTAL (N = 33) | p-Value* |
|---|---|---|---|---|
| No. of Patients | 25 | 8 | 33 | 0.0875 |
| Mean (SD) | 0.4 (0.49) | 0.9 (0.83) | 0.5 (0.62) | |
| Median | 0.0 | 1.0 | 0.0 | |
| (Minimum, Maximum) | (0.0, 1.0) | (0.0, 2.0) | (0.0, 2.0) | |

Pain

Pain scores were reduced for patients treated with dressing assembly 10 (p=0.0993) compared to control. dressing assembly 10 patients treated with periodontal dressing experienced a 67% reduction in pain score compared to control patients.

TABLE 5

Summary of Pain Score by Treatment Group

| Parameter | Control (No dressing Assembly) (N = 15) | Dressing Assembly (N = 33) | TOTAL (N = 48) |
|---|---|---|---|
| Pain Score | | | |
| All Treatment Groups Combined | | | |
| No. of Patients | 15 | 33 | 48 |
| Mean (SD) | 2.9 (1.64) | 2.2 (1.98) | 2.4 (1.89) |
| Median | 3.0 | 1.0 | 2.0 |
| (Minimum, Maximum) | (0.0, 5.0) | (0.0, 8.0) | (0.0, 8.0) |
| Periodontal Dressing | | | |
| No. of Patients | 9 | 25 | 34 |
| Mean (SD) | 2.0 (1.22) | 1.8 (1.82) | 1.9 (1.67) |
| Median | 2.0 | 1.0 | 1.0 |
| (Minimum, Maximum) | (0.0, 4.0) | (0.0, 8.0) | (0.0, 8.0) |
| Solid Stent | | | |
| No. of Patients | 6 | 5 | 11 |
| Mean (SD) | 4.2 (1.33) | 3.6 (2.41) | 3.9 (1.81) |
| Median | 5.0 | 3.0 | 5.0 |
| (Minimum, Maximum) | (2.0, 5.0) | (1.0, 7.0) | (1.0, 7.0) |
| Perforated Stent | | | |
| No. of Patients | 0 | 3 | 3 |
| Mean (SD) | N/A | 3.0 (2.00) | 3.0 (2.00) |
| Median | N/A | 3.0 | 3.0 |
| (Minimum, Maximum) | N/A | (1.0, 5.0) | (1.0. 5.0) |

Soft Tissue Healing

Soft tissue healing was statistically significantly improved for all patients treated with the dental assembly 10 compared to control patients (p<0.0001). Patients treated with the dental assembly using periodontal dressing (p=0.0029) and periodontal stent patients (p=0.0037) all healed statistically significantly better than surgical control patients.

TABLE 6

Summary of Healing Score by Treatment Group

| Parameter | Control (No Dressing Assembly) (N = 15) | Dressing Assembly (N = 33) | TOTAL (N = 48) | p-Value* |
|---|---|---|---|---|
| Healing Score | | | | |
| All Treatment Groups Combined | | | | <0.0001 |
| No. of Patients | 15 | 33 | 48 | |
| Mean (SD) | 1.9 (0.70) | 1.1 (0.33) | 1.4 (0.61) | |
| Median | 2.0 | 1.0 | 1.0 | |
| (Minimum, Maximum) | (1.0, 3.0) | (1.0, 2.0) | (1.0, 3.0) | |
| Periodontal Dressing | | | | 0.0029 |
| No. of Patients | 9 | 25 | 34 | |
| Mean (SD) | 1.6 (0.53) | 1.1 (0.28) | 1.2 (0.41) | |
| Median | 2.0 | 1.0 | 1.0 | |
| (Minimum, Maximum) | (1.0, 2.0) | (1.0, 2.0) | (1.0, 2.0) | |
| Solid & Perforated Stent | | | | 0.0037 |
| No. of Patients | 6 | 8 | 14 | |
| Mean (SD) | 2.5 (0.55) | 1.3 (0.46) | 1.8 (0.80) | |
| Median | 2.5 | 1.0 | 2.0 | |
| (Minimum, Maximum) | (2.0, 3.0) | (1.0, 2.0) | (1.0, 3.0) | |

Free gingival graft palatal donor sites are among the most common surgical wounds produced in periodontal surgery and most heal by secondary intent. Many hemostatic agents have been used to treat these surgical wounds including those that are porcine, bovine or human based materials that all have cultural, religious, biologic and allergic problems associated with their use and which are eliminated using the dressing assembly 10. Further, use of the dressing assembly 10 decreased pain scores (p=0.1120) and inflammation (p=0.0993) for the patients compared to control patients. Hemostasis (p=0.0147) and soft tissue healing (p<0.0001) times were statistically significantly reduced, as well. The dressing assembly 10 is also shown to be bacteriostatic, thereby limiting the growth of bacteria.

II. MANUFACTURE OF THE DENTAL PAD ASSEMBLY

A desirable methodology for making the tissue dressing pad assembly 10 will now be described. This methodology is shown schematically in FIGS. 15, A to H. It should be realized, of course, that other methodologies can be used.

A. Preparation of a Chitosan Solution

The chitosan used to prepare the chitosan solution (designated CS in FIG. 25, Step A) preferably has a fractional degree of deacetylation greater than 0.78 but less than 0.97. Most preferably the chitosan has a fractional degree of deacetylation greater than 0.85 but less than 0.95. Preferably the chitosan selected for processing into the matrix has a viscosity at 25° C. in a 1% (w/w) solution of 1% (w/w) acetic acid (AA) with spindle LVI at 30 rpm, which is about 100 centipoise to about 2000 centipoise. More preferably, the chitosan has viscosity at 25° C. in a 1% (w/w) solution of 1% (w/w) acetic acid (AA) with spindle LVI at 30 rpm, which is about 125 centipoise to about 1000 centipoise. Most preferably, the chitosan has viscosity at 25° C. in a 1% (w/w) solution of 1% (w/w) acetic acid (AA) with spindle LV1 at 30 rpm, which is about 400 centipoise to about 800 centipoise.

Figure 25:
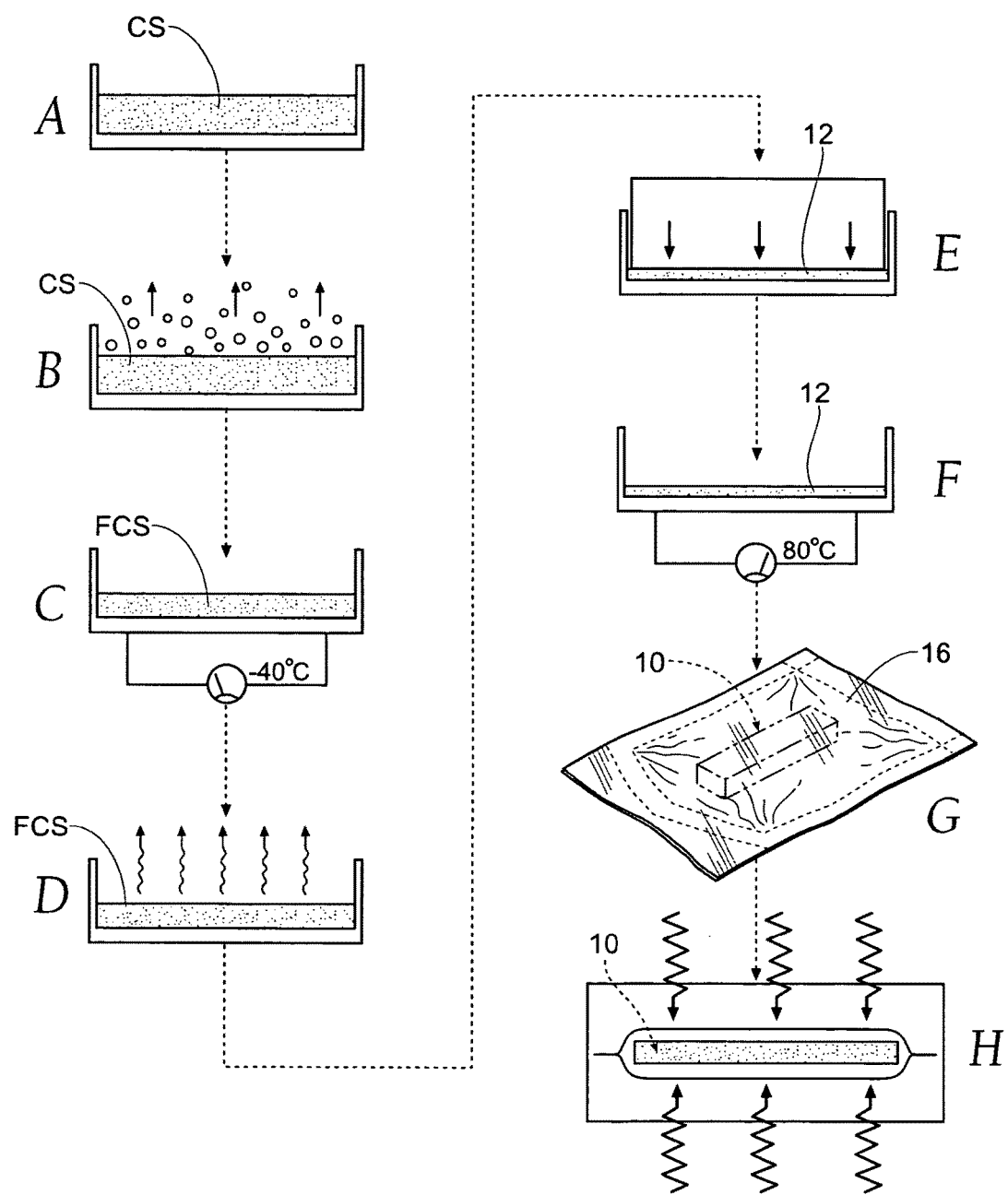
FIG. 25 is a diagrammatic view of the steps of a representative process for creating the dental pad assembly shown in FIG. 6.

The chitosan solution CS is preferably prepared at 25° C. by addition of water to solid chitosan flake or powder and the solid dispersed in the liquid by agitation, stirring or shaking (see FIG. 25, Step A). On dispersion of the chitosan in the liquid, the acid component is added and mixed through the dispersion to cause dissolution of the chitosan solid. The rate of dissolution will depend on the temperature of the solution, the molecular weight of the chitosan and the level of agitation. Preferably the dissolution step is performed within a closed tank reactor with agitating blades or a closed rotating vessel. This ensures homogeneous dissolution of the chitosan and no opportunity for high viscosity residue to be trapped on the side of the vessel. Preferably the chitosan solution percentage (w/w) is greater than 0.5% chitosan and less than 2.7% chitosan. More preferably the chitosan solution percentage (w/w) is greater than 1% chitosan and less than 2.3% chitosan. Most preferably the chitosan solution percentage is greater than 1.5% chitosan and less than 2.1% chitosan. Preferably the acid used is acetic acid. Preferably the acetic acid is added to the solution to provide for an acetic acid solution percentage (w/w) at more than 0.8% and less than 4%. More preferably the acetic acid is added to the solution to provide for an acetic acid solution percentage (w/w) at more than 1.5% (w/w) and less than 2.5%.

The structure or form producing steps for the chitosan matrix 12 are typically carried out from solution and can be accomplished employing techniques such as freezing (to cause phase separation), non-solvent die extrusion (to produce a filament), electro-spinning (to produce a filament), phase inversion and precipitation with a non-solvent (as is typically used to produce dialysis and filter membranes) or solution coating onto a preformed sponge-like or woven product. In the case of freezing, where two or more distinct phases are formed by freezing (typically water freezing into ice with differentiation of the chitosan biomaterial into a separate solid phase), another step is required to remove the frozen solvent (typically ice), and hence produce the chitosan matrix 12 without disturbing the frozen structure. This may be accomplished by a freeze-drying and/or a freeze substitution step. The filament can be formed into a non-woven sponge-like mesh by non-woven spinning processes. Alternately, the filament may be produced into a felted weave by conventional spinning and weaving processes. Other processes that may be used to make the biomaterial sponge-like product include dissolution of added porogens from a solid chitosan matrix 12 or boring of material from said matrix.

B. Degassing the Aqueous Chitosan Solution

Preferably (see FIG. 25, Step B), the chitosan biomaterial solution CS is degassed of general atmospheric gases. Typically, degassing is removing sufficient residual gas from the chitosan biomaterial solution CS so that, on undergoing a subsequent freezing operation, the gas does not escape and form unwanted large voids or large trapped gas bubbles in the subject wound dressing product. The degassing step may be performed by heating a chitosan biomaterial, typically in the form of a solution CS, and then applying a vacuum thereto. For example, degassing can be performed by heating a chitosan solution to about 45° C. immediately prior to applying vacuum at about 500 mTorr for about 5 minutes while agitating the solution.

In one embodiment, certain gases can be added back into the solution to controlled partial pressures after initial degassing. Such gases would include but are not limited to argon, nitrogen and helium. An advantage of this step is that solutions containing partial pressures of these gases form microvoids on freezing. The microvoid is then carried through the sponge as the ice-front advances. This leaves a well defined and controlled channel that aids sponge pore interconnectivity.

C. Freezing the Aqueous Chitosan Solution

Next (see FIG. 25, Step C), the chitosan biomaterial—which is typically now in acid solution and degassed, as described above—is subjected to a freezing step. Freezing is preferably carried out by cooling the chitosan biomaterial solution supported within a mold and lowering the solution temperature from room temperature to a final temperature below the freezing point. More preferably this freezing step is performed on a plate freezer whereby a thermal gradient is introduced through the chitosan solution in the mold by loss of heat through the plate cooling surface. Preferably this plate cooling surface is in good thermal contact with the mold. Preferably the temperature of the chitosan solution and mold before contact with the plate freezer surface is are near room temperature. Preferably the plate freezer surface temperature is not more than −10° C. before introduction of the mold+ solution. Preferably the thermal mass of the mold+solution is less than the thermal mass of the plate freezer shelf+heat transfer fluid. Preferably the molds are formed from, but are not limited to, a metallic element such as iron, nickel, silver, copper, aluminum, aluminum alloy, titanium, titanium alloy, vanadium, molybdenum, gold, rhodium, palladium, platinum and/or combinations thereof. The molds may also be coated with thin, inert metallic coatings such as titanium, chromium, tungsten, vanadium, nickel, molybdenum, gold and platinum in order to ensure there is no reaction with the acid component of the chitosan solution and the chitosan salt matrix. Thermally insulating coatings or elements may be used in conjunction with the metallic molds to control heat transfer in the molds. Preferably the mold surfaces do not bind with the frozen chitosan solution. The inside surface of the mold is preferably coated with a thin, permanently-bound, fluorinated release.coating formed from polytetrafluoroethylene (PTFE) (TEFLON®), fluorinated ethylene polymer (FEP), or other fluorinated polymeric materials. Although coated metallic molds are preferable, thin walled plastic molds can be a convenient alternative for supporting the solution. Such plastic molds would include, but not be limited to, molds prepared by injection molding, machining or thermoforming from polyvinylchloride, polystyrene, acrylonitrile-butadiene-styrene copolymers, polyesters, polyamides, polyurethanes and polyolefins. An advantage of the metallic molds combined with local placement of thermally insulating elements is that they also provide opportunity for improved control of heat flow and structure within the freezing sponge. This improvement in heat flow control results from large thermal conductivity differences between thermally conducting and thermally insulating element placements in the mold.

Freezing of the chitosan solution in this way (forming a frozen chitosan solution, designed FCS in FIG. 15, Step C) enables the preferred structure of the pad assembly product to be prepared.

The plate freezing temperature affects the structure and mechanical properties of the final chitosan matrix 12. The plate freezing temperature is preferably not higher than about −10° C., more preferably not more than about −20° C., and most preferably not more than about −30° C. When frozen at −10° C., the structure of the uncompressed chitosan matrix 12 is very open and vertical throughout the open sponge structure. When frozen at −25° C., the structure of the uncompressed chitosan matrix 12 is more closed, but it is still vertical. When frozen at −40° C., the structure of the uncompressed chitosan matrix 12 is closed and not vertical. Instead, the chitosan matrix 12 comprises more of a reinforced, inter-meshed structure. The adhesive/cohesive sealing properties of the chitosan matrix 12 are observed to improve as lower freezing temperatures are used. A freezing temperatures of about −40° C. forms a structure for the chitosan matrix 12 having superior adhesive/cohesive properties.

During the freezing step, the temperature may be lowered over a predetermined time period. For example, the freezing temperature of a chitosan biomaterial solution may be lowered from room temperature to −45° C. by plate cooling application of a constant temperature cooling ramp of between about −0.4° C./mm to about −0.8° C./mm for a period of about 90 minutes to about 160 minutes.

D. Freeze Drying the Chitosan/Ice Matrix

The frozen chitosan/ice matrix (FCS) desirably undergoes water removal from within the interstices of the frozen material (see FIG. 25, Step D). This water removal step may be achieved without damaging the structural integrity of the frozen chitosan biomaterial FCS. This may be achieved without producing a liquid phase, which can disrupt the structural arrangement of the ultimate chitosan matrix 12. Thus, the ice in the frozen chitosan biomaterial FSC passes from a solid frozen phase into a gas phase (sublimation) without the formation of an intermediate liquid phase. The sublimated gas is trapped as ice in an evacuated condenser chamber at substantially lower temperature than the frozen chitosan biomaterial.

The preferred manner of implementing the water removal step is by freeze-drying, or lyophilization. Freeze-drying of the frozen chitosan biomaterial FCS can be conducted by further cooling the frozen chitosan biomaterial. Typically, a vacuum is then applied. Next, the evacuated frozen chitosan material may be gradually heated.

More specifically, the frozen chitosan biomaterial may be subjected to subsequent freezing preferably at about −15° C., more preferably at about −25° C., and most preferably at about −45° C., for a preferred time period of at least about 1 hour, more preferably at least about 2 hour, and most preferably at least about 3 hour. This step can be followed by cooling of the condenser to a temperature of less than about −45° C., more preferably at about −60° C., and most preferably at about −85° C. Next, a vacuum in the amount of preferably at most about 100 mTorr, more preferably at most about 150 mTorr, and most preferably at least about 200 mTorr, can be applied. The evacuated frozen chitosan material can be heated preferably at about −25° C., more preferably at about −15° C., and most preferably at about −10° C., for a preferred time period of at least about 1 hour, more preferably at least about 5 hour, and most preferably at least about 10 hour.

Further freeze drying, maintaining vacuum pressure at near 200 mTorr, is conducted at a shelf temperature of about 20° C., more preferably at about 15° C., and most preferably at about 10° C., for a preferred time period of at least about 36 hours, more preferably at least about 42 hours, and most preferably at least about 48 hours.

E. Densification of the Chitosan Matrix

The chitosan matrix before densification (density near 0.03 g/cm$^3$) will be called an "uncompressed chitosan matrix." This uncompressed matrix is not ideal in stanching bleeding, since it may rapidly dissolve in blood and possess poor mechanical properties. The chitosan biomaterial is therefore desirably compressed (see FIG. 10, Step E). Compression loading normal to the hydrophilic matrix polymer surface with heated platens can be used to compress the dry "uncompressed" chitosan matrix 12 to reduce the thickness and increase the density of the matrix. The compression step, which will sometimes be called in shorthand "densification," significantly increases adhesion strength, cohesion strength and dissolution resistance of the chitosan matrix 12. Appropriately frozen chitosan matrices 12 compressed above a threshold density (close to 0.1 g/cm$^3$) do not readily dissolve in flowing blood at 37° C.

The compression temperature is preferably not less than about 60° C., more preferably it is not less than about 75° C. and not more than about 85° C.

After densification, the density of the matrix 12 can be different at the base ("active") surface of the matrix 12 (i.e., the surface exposed to tissue) than at the top surface of the matrix 12. For example, in a typical matrix 12 where the mean density measured at the active surface is at or near the most preferred density value of 0.2 g/cm$^3$, the mean density measured at the top surface can be significantly lower, e.g., at 0.05 g/cm$^3$. The desired density ranges as described herein for a densified matrix 12, are intended to exist at are near the active side of the matrix 12, where exposure to blood, fluid, or moisture first occurs.

The densified chitosan biomaterial is next preferably preconditioned by heating chitosan matrix 12 in an oven to a temperature of preferably up to about 75° C., more preferably to a temperature of up to about 80° C., and most preferably to a temperature of preferably up to about 85° C. (FIG. 25, Step F). Preconditioning is typically conducted for a period of time up to about 0.25 hours, preferably up to about 0.35 hours, more preferably up to about 0.45 hours, and most preferably up to about 0.50 hours. This pre-conditioning step provides further significant improvement in dissolution resistance with a small cost in a 20-30% loss of adhesion properties.

F. Placement in the Pouch

The tissue dressing pad assembly 10 can be subsequently packaged in the pouch 16 (see FIG. 25, Step F), either in a precut size or as a source pad assembly 11. The pouch 16 is desirably purged with an inert gas such as either argon or nitrogen gas, evacuated and heat sealed. The pouch 16 acts to maintain interior contents sterility over an extend time (at least 24 months) and also provides a very high barrier to moisture and atmospheric gas infiltration over the same period.

G. Sterilization

After pouching, the processed tissue dressing pad assembly 10 is desirably subjected to a sterilization step (see FIG. 25, Step G). The tissue dressing pad assembly 10 can be sterilized by a number of methods. For example, a preferred method is by irradiation, such as by gamma irradiation, which can further enhance the blood dissolution resistance, the tensile properties and the adhesion properties of the wound dressing. The irradiation can be conducted at a level of at least about 5 kGy, more preferably a least about 10 kGy, and most preferably at least about 15 kGy.

H. Improving Compliance and Flexibility

Bending and/or molding of the pad assembly 10 prior to placement on the targeted treatment of injury site has been already described and recommended. In hydrophilic polymer sponge structures, of which the pad assembly 10 is but one example, the more flexible and compliant the structure is, the more resistant it is to tearing and fragmentation as the structure is made to conform to the shape of the targeted treatment site and achieve apposition of the sponge structure with the underlying (typically) irregular surface of the injury. Resistance to tearing and fragmentation is a benefit, as it maintains wound sealing and hemostatic efficacy. Improved compliance and flexibility can be achieved by mechanical manipulation of any hydrophilic polymer sponge structure during or after manufacture, without loss of beneficial features of robustness and longevity of resistance to dissolution.

There are several ways in which such mechanical manipulation can be accomplished during or after manufacture; for example, (i) by controlled micro-fracturing of the substructure of a hydrophilic polymer sponge structure by rolling, bending, twisting, rotating, vibrating, probing, compressing, extending, shaking and kneading; (ii) controlled macro-texturing (by the formation of deep relief patterns) in a given hydrophilic polymer sponge structure by thermal compression techniques at 80° C.; and (iii) by controlled formation of vertical channels into a given hydrophilic polymer sponge structure during the freezing step of the sponge structure preparation, or alternatively it may be achieved mechanically by perforation of the sponge structure during the compression (densification) step.

Further details of mechanical manipulations that can be performed to improve compliance and flexibility are shown in co-pending U.S. patent application Ser. No. 11/020,365, filed Dec. 23, 2004, and entitled "Tissue Dressing Assemblies, Systems, and Methods Formed From Hydrophilic Polymer Sponge Structures Such as Chitosan," which is incorporated herein by reference.

III. ALTERNATIVE EMBODIMENTS

The dental pad assembly 10 can be provided in various alternative forms.

Figure 26A:
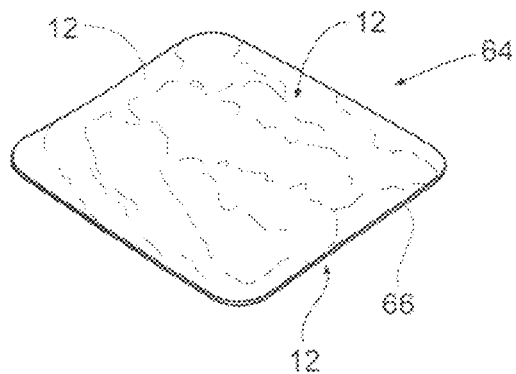
FIGS. 26A and 26B are, respectively, a perspective assembled view and a perspective exploded view of an alternative embodiment of a dental pad assembly for treating tissue or bone in an oral cavity or an adjacent anatomic structure, comprising a hydrophilic polymer sponge structure incorporated into a tissue dressing sheet assembly.
Figure 26B:
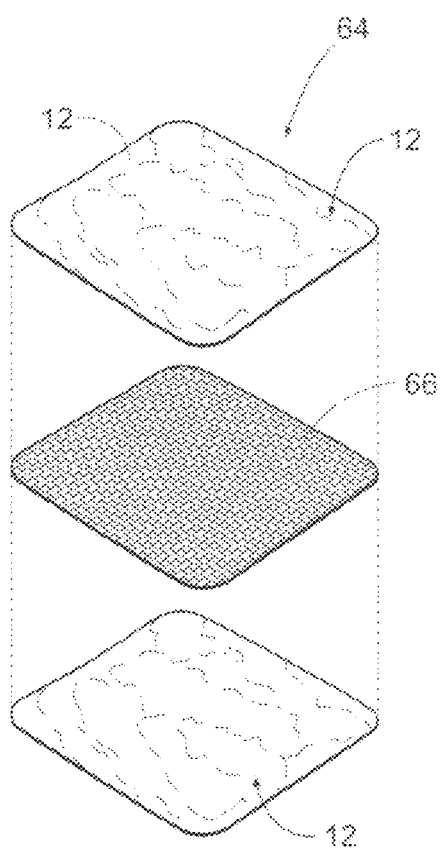
Figure 26C:
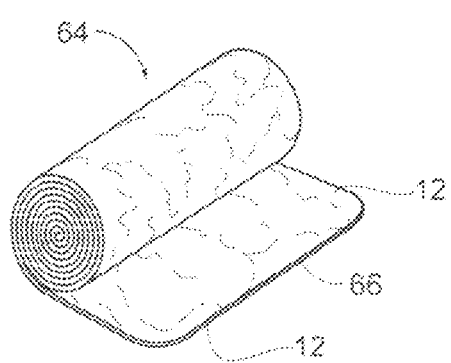
FIG. 26C is a perspective view of the tissue dressing sheet assembly being shaped and configured into a roll form for placement into contact with tissue or bone in an oral cavity or an adjacent anatomic structure.

For example, as shown in FIGS. 26A and 26B, a pad assembly 64 can comprise a sheet 66 of woven or non-woven mesh material enveloped between layers of the tissue dressing matrix 12. The tissue dressing matrix 12 impregnates the sheet 66. The size, shape, and configuration of the tissue dressing sheet assembly 64 can vary according to its intended use. The sheet pad assembly 64 can be rectilinear, elongated, square, round, oval, or composite or complex combinations thereof. The tissue dressing sheet assembly 64 is preferably thin (compared to the pad assembly 10), being in the range of between 0.5 mm to 1.5 mm in thickness. A preferred form of the thin reinforced structure of the sheet assembly 64 comprises a chitosan matrix 12 or sponge, at the typical chitosan matrix density of 0.10 to 0.20 g/cm3, reinforced by absorbable bandage webbing such as cotton gauze and the resultant bandage thickness is 1.5 mm or less. The sheet 66 can comprise woven and non-woven mesh materials, formed, e.g., from cellulose derived material such as gauze cotton mesh. The sheet assembly 64 accommodates layering, compaction, and/or rolling—i.e., "stuffing" (as FIG. 26C shows)—of the hydrophilic polymer sponge structure (e.g., the chitosan matrix 12) within a wound site using pressure to further reinforce the overall structure against arterial and venous bleeding. By stuffing of the sheet structure over itself, as FIG. 26C shows, the interaction of the blood with the hydrophilic polymer (e.g., chitosan) infused within the webbing provides for a highly adhesive, insoluble and highly conforming packing form.

Further details of the sheet assembly 64 can be founding in co-pending U.S. patent application Ser. No. 11/020,365, filed Dec. 23, 2004, and entitled "Tissue Dressing Assemblies, Systems, and Methods Formed From Hydrophilic Polymer Sponge Structures Such as Chitosan," which is incorporated herein by reference.

IV. FURTHER USES

The dental assembly of the present invention can also provide a topically applied platform for the delivery of one or more therapeutic agents into the blood stream in a controlled release fashion. The therapeutic agents can be incorporated into the hydrophilic polymer sponge structure, e.g., either before or after the freezing step, and before the drying and densification steps, as will be described later. Examples of therapeutic agents that can be incorporated into a hydrophilic polymer sponge structure (e.g., the chitosan matrix 12) include, but are not limited to, drugs or medications, stem cells, antibodies, anti-microbials, anti-virals, collagens, genes, DNA, and other therapeutic agents; hemostatic agents like fibrin; growth factors; Bone Morphogenic Protein (BMP); peptides; STAMPS; DNA vaccines and similar compounds.

V. CONCLUSION

It has been demonstrated that a hydrophilic polymer sponge structure like the chitosan matrix 12 can be readily adapted for association with dressings or platforms of various sizes and configurations in association with dental procedures or trauma involving the oral cavity—in pad form, in sheet form, or in otherwise compliant form. The dental assembly 10 of the present invention also provides improved hemostasis and healing capabilities at free gingival graft palatal donor sites.

Therefore, it should be apparent that above-described embodiments of this invention are merely descriptive of its principles and are not to be limited. The scope of this invention instead shall be determined from the scope of the following claims, including their equivalents.

We claim:
1. A compliant hydrophilic polymer sponge structure having a moisture content of 5% moisture or less and shaped, sized, and configured for use in periodontal free gingival graft structural procedures;
   wherein the hydrophilic sponge structure has been densified by compression prior to use to a density of between 0.6 to 0.1 g/cm$^3$ and comprises a chitosan biomaterial that is not crosslinked and forms an adhesive in situ upon contact with any one of blood, fluid, and moisture.
2. A structure according to claim 1 wherein said structure further promotes soft tissue healing.
3. A structure according to claim 1 wherein said structure further promotes bone healing.
4. A structure according to claim 1 wherein said structure further comprises a platform for the delivery of a therapeutic agent.
5. A method comprising placing the hydrophilic polymer sponge of claim 1 within a periodontal wound site.
6. An assembly for use in a periodontal procedure for treating a wound site, said assembly comprising:
   a compliant hydrophilic sponge structure densified by compression prior to use to a density of between 0.6 to 0.1 g/cm$^3$, having a moisture content of 5% moisture or less, and comprising a chitosan material that is not crosslinked, wherein the sponge is capable of being applied to said wound site, and forming an adhesive in situ upon contact with any one of blood, fluid, and moisture; and
   a structure for covering the sponge structure;
   wherein the structure for covering the sponge structure comprises a stent.
7. The structure according to claim 1 wherein the compliant hydrophilic polymer sponge structure comprising a chitosan biomaterial further comprises at least one of glutamic acid, lactic acid, formic acid, hydrochloric acid, and acetic acid.
8. The structure according to claim 1 wherein the compliant hydrophilic polymer sponge structure comprising a chitosan biomaterial further comprises one of hydrochloric acid and acetic acid.
9. The structure according to claim 1 wherein the compliant hydrophilic polymer sponge structure comprising a chitosan biomaterial further comprises a medication or physiologic or pharmacologic agent that acts locally or systemically in the body.
10. The structure according to claim 9 wherein the medication or physiologic or pharmacologic agent is at least one of enzymes, organic catalysts, ribozymes, organometallics, proteins, glycoproteins, peptides, polyamino acids, antibodies, nucleic acids, steroidal molecules, antibiotics, antimycotics, cytokines, growth factors for tissue and/or bone, carbohydrates, oleophobics, lipids, extracellular matrix and/or individual components, mammalian cells, stem cells, genetically engineered cells, pharmaceuticals, and therapeutics.
11. The structure according to claim 1 wherein the compliant hydrophilic polymer sponge structure comprising a chitosan biomaterial has been densified by heat compression at a temperature between about 60° C. and 85° C.
12. The structure according to claim 1 wherein the compliant hydrophilic polymer sponge structure comprising a chitosan biomaterial has been densified by compression prior to use to a density of 0.20 g/cm3.
13. The structure according to claim 12 wherein the compliant hydrophilic polymer sponge structure comprising a chitosan biomaterial has been densified by heat compression at a temperature between about 60° C. and 85° C.

14. The structure according to claim 1 wherein the compliant hydrophilic polymer sponge structure comprising a chitosan biomaterial is mechanically manipulated for improved compliance and flexibility.

15. The structure according to claim 6 wherein the compliant hydrophilic polymer sponge structure comprising a chitosan biomaterial is mechanically manipulated for improved compliance and flexibility.

16. The structure according to claim 1 wherein the compliant hydrophilic polymer sponge structure comprising a chitosan biomaterial is preconditioned at a temperature between about 75° C. and about 85° C.

* * * * *